(12) United States Patent
Hoffer

(10) Patent No.: US 9,566,436 B2
(45) Date of Patent: Feb. 14, 2017

(54) TRANSVASCULAR NERVE STIMULATION APPARATUS AND METHODS

(71) Applicant: Simon Fraser University, Burnaby (CA)

(72) Inventor: Joaquin Andres Hoffer, Anmore (CA)

(73) Assignee: Simon Fraser University, Burnaby, British Columbia (CA)

( * ) Notice: Subject to any disclaimer, the term of this patent is extended or adjusted under 35 U.S.C. 154(b) by 0 days.

(21) Appl. No.: 14/792,006

(22) Filed: Jul. 6, 2015

(65) Prior Publication Data

US 2015/0306397 A1 Oct. 29, 2015

Related U.S. Application Data

(63) Continuation of application No. 14/448,734, filed on Jul. 31, 2014, now Pat. No. 9,108,059, which is a continuation of application No. 14/044,466, filed on Oct. 2, 2013, now Pat. No. 9,220,898, which is a continuation of application No. 12/524,571, filed as

(60) Provisional application No. 60/887,031, filed on Jan. 29, 2007.

(Continued)

(51) Int. Cl.
*A61N 1/36* (2006.01)
*A61N 1/05* (2006.01)

(52) U.S. Cl.
CPC ............... *A61N 1/3611* (2013.01); *A61N 1/05* (2013.01); *A61N 1/0551* (2013.01); *A61N 1/0558* (2013.01); *A61N 1/3601* (2013.01); *A61N 1/36139* (2013.01); *A61N 1/36185* (2013.01)

(58) Field of Classification Search
CPC ..... A61N 1/056; A61N 1/3605; A61N 1/0551
See application file for complete search history.

(56) References Cited

U.S. PATENT DOCUMENTS 3,769,984 A 11/1973 Muench
3,835,864 A 9/1974 Rasor et al.
4,643,201 A 2/1987 Stokes
(Continued)

FOREIGN PATENT DOCUMENTS

EP 9964105 A1 12/1999
EP 0993840 A1 4/2000
(Continued)

OTHER PUBLICATIONS

Schauerte, P. et al., "Transvenous Parasympathetic Cardiac Nerve Stimulation: an approach for stable sinus rate control", Journal of Cardiovascular Electrophysiology 10(11): 1517-1524, Nov. 1999.

(Continued)

*Primary Examiner* — Christopher D Koharski
*Assistant Examiner* — Natasha Patel
(74) *Attorney, Agent, or Firm* — Bookoff McAndrews, PLLC

(57) ABSTRACT

Electrode structures for transvascular nerve stimulation combine electrodes with an electrically-insulating backing layer. The backing layer increases the electrical impedance of electrical paths through blood in a lumen of a blood vessel and consequently increases the flow of electrical current through surrounding tissues. The electrode structures may be applied to stimulate nerves such as the phrenic, vagus, trigeminal, obturator or other nerves.

24 Claims, 16 Drawing Sheets

Related U.S. Application Data application No. PCT/CA2008/000179 on Jan. 29, 2008, now Pat. No. 8,571,662.

(56) References Cited

U.S. PATENT DOCUMENTS

| | | |
|---|---|---|
| 5,056,519 A | 10/1991 | Vince |
| 5,146,918 A | 9/1992 | Kallok et al. |
| 5,170,802 A | 12/1992 | Mehra |
| 5,224,491 A | 7/1993 | Mehra |
| 5,330,522 A | 7/1994 | Kreyenhagen |
| 5,417,208 A | 5/1995 | Winkler |
| 5,465,717 A | 11/1995 | Imran et al. |
| 5,476,498 A | 12/1995 | Ayers |
| 5,678,535 A | 10/1997 | DiMarco |
| 5,755,765 A | 5/1998 | Hyde et al. |
| 5,779,732 A | 7/1998 | Amundson |
| 5,785,706 A | 7/1998 | Bednarek |
| 5,824,027 A | 10/1998 | Hoffer et al. |
| 5,954,761 A | 9/1999 | Mahchek et al. |
| 6,006,134 A | 12/1999 | Hill et al. |
| 6,120,476 A | 9/2000 | Fung et al. |
| 6,136,021 A | 10/2000 | Tockman et al. |
| 6,157,862 A | 12/2000 | Brownlee et al. |
| 6,161,029 A | 12/2000 | Spreigl et al. |
| 6,201,994 B1 | 3/2001 | Warman et al. |
| 6,212,435 B1 | 4/2001 | Lattner et al. |
| 6,240,320 B1 | 5/2001 | Spehr et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,584,362 B1 | 6/2003 | Scheiner et al. |
| 6,682,526 B1 | 1/2004 | Jones et al. |
| 6,718,208 B2 | 4/2004 | Hill et al. |
| 6,778,854 B2 | 8/2004 | Puskas |
| 6,885,888 B2 | 4/2005 | Rezai |
| 6,907,285 B2 | 6/2005 | Denker et al. |
| 6,934,583 B2 | 8/2005 | Weinberg et al. |
| 7,072,720 B2 | 7/2006 | Puskas |
| 7,082,331 B1 | 7/2006 | Park et al. |
| 7,142,903 B2 | 11/2006 | Rodriguez et al. |
| 7,149,585 B2 | 12/2006 | Wessman et al. |
| 7,184,829 B2 | 2/2007 | Hill et al. |
| 7,225,016 B1 | 5/2007 | Koh |
| 7,225,019 B2 | 5/2007 | Jahns et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,421,296 B1 | 9/2008 | Benser et al. |
| 7,519,426 B1 | 4/2009 | Koh et al. |
| 7,591,265 B2 | 9/2009 | Lee et al. |
| 7,636,600 B1 | 12/2009 | Koh |
| 7,672,728 B2 | 3/2010 | Libbus et al. |
| 7,672,729 B2 | 3/2010 | Koh et al. |
| 7,676,275 B1 | 3/2010 | Farazi et al. |
| 7,783,362 B2 | 8/2010 | Whitehurst et al. |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,891,085 B1 | 2/2011 | Kuzma et al. |
| 7,925,352 B2 | 4/2011 | Stack et al. |
| 7,962,215 B2 | 6/2011 | Ignagni et al. |
| 7,970,475 B2 | 6/2011 | Tehrani et al. |
| 7,979,128 B2 | 7/2011 | Tehrani et al. |
| 8,036,750 B2 | 10/2011 | Caparso et al. |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,233,987 B2 | 7/2012 | Gelfand et al. |
| 8,244,358 B2 | 8/2012 | Tehrani et al. |
| 8,244,359 B2 | 8/2012 | Gelfand et al. |
| 8,255,056 B2 | 8/2012 | Tehrani |
| 8,256,419 B2 | 9/2012 | Sinderby et al. |
| 8,265,759 B2 | 9/2012 | Tehrani et al. |
| 8,280,513 B2 | 10/2012 | Tehrani et al. |
| 8,335,567 B2 | 12/2012 | Tehrani et al. |
| 8,348,941 B2 | 1/2013 | Tehrani |
| 8,369,954 B2 | 2/2013 | Stack et al. |
| 8,401,640 B2 | 3/2013 | Zhao et al. |
| 8,401,651 B2 | 3/2013 | Caparso et al. |
| 8,406,885 B2 | 3/2013 | Ignagni et al. |
| 8,412,331 B2 | 4/2013 | Tehrani et al. |
| 8,428,711 B2 | 4/2013 | Lin et al. |
| 8,428,726 B2 | 4/2013 | Ignagni et al. |
| 8,433,412 B1 | 4/2013 | Westlund et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,483,834 B2 | 7/2013 | Lee et al. |
| 8,504,158 B2 | 8/2013 | Karamanoglu et al. |
| 8,509,901 B2 | 8/2013 | Tehrani |
| 8,509,902 B2 | 8/2013 | Cho et al. |
| 8,509,919 B2 | 8/2013 | Yoo et al. |
| 8,522,779 B2 | 9/2013 | Lee et al. |
| 8,560,072 B2 | 10/2013 | Caparso et al. |
| 8,617,228 B2 | 12/2013 | Wittenberger et al. |
| 8,620,450 B2 | 12/2013 | Tockman et al. |
| 8,626,292 B2 | 1/2014 | McCabe et al. |
| 8,630,707 B2 | 1/2014 | Zhao et al. |
| 8,676,323 B2 | 3/2014 | Ignagni et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,755,889 B2 | 6/2014 | Scheiner |
| 8,781,578 B2 | 7/2014 | McCabe et al. |
| 8,781,582 B2 | 7/2014 | Ziegler et al. |
| 8,781,583 B2 | 7/2014 | Cornelussen et al. |
| 8,838,245 B2 | 9/2014 | Lin et al. |
| 8,897,879 B2 | 11/2014 | Karamanoglu et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,942,824 B2 | 1/2015 | Yoo et al. |
| 9,042,981 B2 | 5/2015 | Yoo et al. |
| 2001/0052345 A1 | 12/2001 | Niazi |
| 2002/0026228 A1 | 2/2002 | Schauerte |
| 2002/0065544 A1 | 5/2002 | Smits |
| 2002/0128546 A1 | 9/2002 | Silver |
| 2002/0188325 A1 | 12/2002 | Hill et al. |
| 2003/0195571 A1 | 10/2003 | Burnes et al. |
| 2004/0010303 A1 | 1/2004 | Bolea et al. |
| 2004/0088015 A1 | 5/2004 | Casavant et al. |
| 2004/0111139 A1 | 6/2004 | McCreery |
| 2004/0186543 A1 | 9/2004 | King et al. |
| 2004/0210261 A1 | 10/2004 | King et al. |
| 2005/0043765 A1 | 2/2005 | Williams et al. |
| 2005/0070981 A1 | 3/2005 | Verma |
| 2005/0085865 A1 | 4/2005 | Tehrani |
| 2005/0096710 A1 | 5/2005 | Kieval |
| 2005/0138791 A1 | 6/2005 | Black et al. |
| 2005/0143787 A1 | 6/2005 | Boreja et al. |
| 2005/0165457 A1 | 7/2005 | Benser et al. |

(56) References Cited

U.S. PATENT DOCUMENTS

| | | |
|---|---|---|
| 2005/0187584 A1 | 8/2005 | Denker et al. |
| 2005/0251238 A1 | 11/2005 | Wallace et al. |
| 2005/0251239 A1 | 11/2005 | Wallace et al. |
| 2005/0288730 A1 | 12/2005 | Deem et al. |
| 2006/0058852 A1 | 3/2006 | Koh et al. |
| 2006/0074449 A1 | 4/2006 | Denker et al. |
| 2006/0149334 A1 | 7/2006 | Tehrani et al. |
| 2006/0188325 A1 | 8/2006 | Dolan |
| 2006/0195159 A1* | 8/2006 | Bradley ............ A61N 1/36132 607/48 |
| 2006/0229677 A1 | 10/2006 | Moffitt et al. |
| 2006/0253161 A1 | 11/2006 | Libbus et al. |
| 2006/0253182 A1* | 11/2006 | King .................... A61N 1/0551 607/117 |
| 2006/0259107 A1 | 11/2006 | Caparso et al. |
| 2007/0027448 A1 | 2/2007 | Paul et al. |
| 2007/0093875 A1 | 4/2007 | Chavan et al. |
| 2007/0106357 A1 | 5/2007 | Denker et al. |
| 2007/0168007 A1 | 7/2007 | Kuzma et al. |
| 2007/0173900 A1* | 7/2007 | Siegel ................ A61B 17/3468 607/41 |
| 2007/0203549 A1 | 8/2007 | Demarais et al. |
| 2007/0208388 A1 | 9/2007 | Jahns et al. |
| 2007/0255379 A1* | 11/2007 | Williams .......... A61M 5/14276 607/120 |
| 2007/0288076 A1 | 12/2007 | Bulkes et al. |
| 2008/0161878 A1 | 7/2008 | Tehrani et al. |
| 2008/0177347 A1 | 7/2008 | Tehrani et al. |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0036947 A1 | 2/2009 | Westlund et al. |
| 2010/0114227 A1 | 5/2010 | Cholette |
| 2010/0268311 A1 | 10/2010 | Cardinal et al. |
| 2011/0230932 A1 | 9/2011 | Tehrani et al. |
| 2011/0288609 A1 | 11/2011 | Tehrani et al. |
| 2012/0053654 A1 | 3/2012 | Tehrani et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0030497 A1 | 1/2013 | Karamanoglu et al. |
| 2013/0158625 A1 | 6/2013 | Gelfand et al. |
| 2013/0165989 A1 | 6/2013 | Gelfand et al. |
| 2013/0197601 A1 | 8/2013 | Tehrani et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0333696 A1 | 12/2013 | Lee et al. |
| 2014/0088580 A1 | 3/2014 | Wittenberger et al. |
| 2014/0114371 A1 | 4/2014 | Westlund et al. |
| 2014/0128953 A1 | 5/2014 | Zhao et al. |
| 2014/0316486 A1 | 10/2014 | Zhou et al. |
| 2014/0324115 A1 | 10/2014 | Ziegler et al. |
| 2015/0034081 A1 | 2/2015 | Tehrani et al. |
| 2015/0045848 A1 | 2/2015 | Cho et al. |
| 2015/0119950 A1 | 4/2015 | Demmer et al. |

FOREIGN PATENT DOCUMENTS

| | | |
|---|---|---|
| EP | 1304135 A2 | 4/2003 |
| FR | 2801509 A1 | 6/2001 |
| WO | WO 9407564 A2 | 4/1994 |
| WO | WO 9965561 A1 | 12/1999 |
| WO | WO 0100273 A1 | 1/2001 |
| WO | WO 02058785 A1 | 8/2002 |
| WO | WO 2006110338 A1 | 10/2006 |
| WO | WO 2006115877 A1 | 11/2006 |
| WO | WO 2007053508 A1 | 5/2007 |

OTHER PUBLICATIONS

Schauerte, P. et al., "Transvenous Parasympathetic Nerve Stimulation in the Inferior Vena Cava and Atrioventricular Conduction", Journal of Cardiovascular Electrophysiology 11(1): 64-69, Jan. 2000.

Planas et al., "Diaphragmatic Pressures: Transvenous vs. direct phrenic nerve stimulation", J. Appl. Physiol. 59(1): 269-273, 1985.

Nabutovsky, Yelena M.S. et al., "Lead Design and Initial Applications of a New Lead for Long-Term Endovascular Vagal Stimulation", PACE 30(1): S215-S218, Jan. 2007.

Pavlovic, D. et al, "Diaphragm pacing during prolonged mechanical ventilation of the lungs could prevent from respiratory muscle fatigue", Medical Hypotheses, 2003, vol. 60, No. 3, pp. 398-403.

* cited by examiner

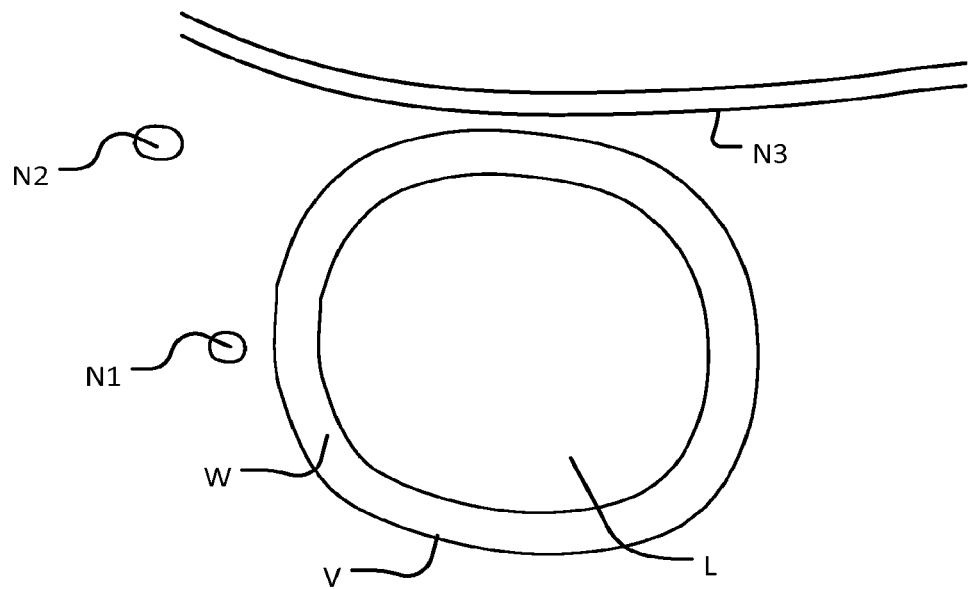
FIGURE 1 - PRIOR ART
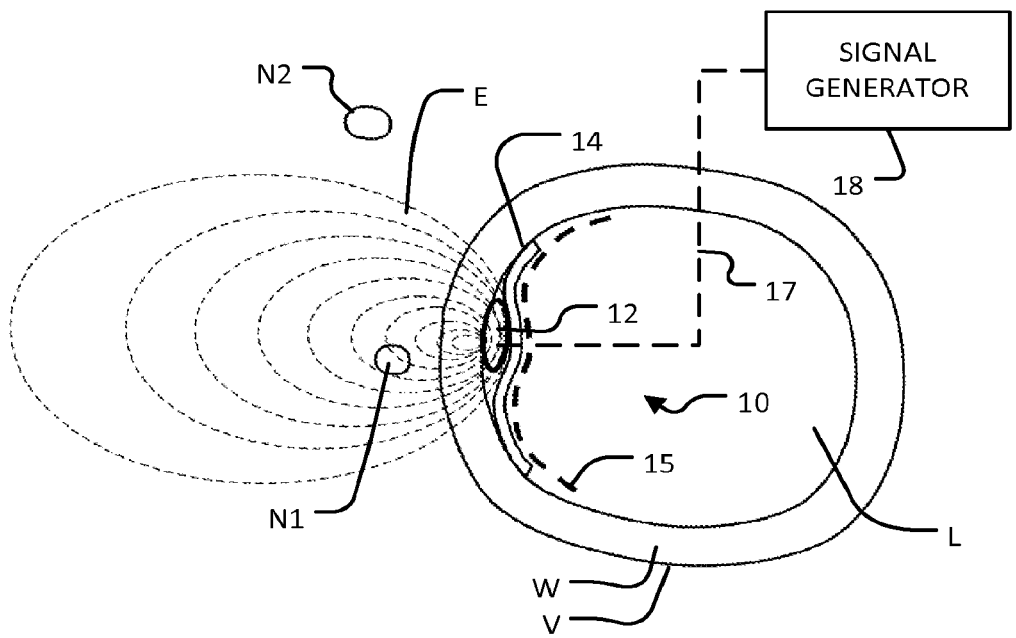
FIGURE 2

TRANSVASCULAR NERVE STIMULATION APPARATUS AND METHODS

CROSS REFERENCE TO RELATED APPLICATION

This application is a continuation application of U.S. patent application Ser. No. 14/448,734, filed Jul. 31, 2014, which is a continuation application of U.S. patent application Ser. No. 14/044,466, filed Oct. 2, 2013, which is a continuation application of U.S. patent application Ser. No. 12/524,571, filed Jul. 25, 2009, now U.S. Pat. No. 8,571,662, issued Oct. 29, 2013, which is a 371 of PCT Patent Application No. PCT/CA2008/000179, filed Jan. 29, 2008, which claims priority from U.S. Provisional Patent Application No. 60/887,031, filed Jan. 29, 2007. The entirety of each of the above applications is incorporated herein by reference.

TECHNICAL FIELD

The invention relates to neurophysiology and in particular to apparatus and methods for stimulating nerves through the walls of blood vessels. Aspects of the invention provide electrode structures that may be deployed within blood vessels to stimulate nerves passing near the blood vessels; nerve stimulation systems; and methods for nerve stimulation. Aspects of the invention may be applied for restoring breathing, treating conditions such as chronic pain, and other uses involving nerve stimulation. Aspects of the invention may be applied in the treatment of acute or chronic conditions.

BACKGROUND

Nerve stimulation can be applied in the treatment of a range of conditions. The nerve stimulation may be applied to control muscle activity or to generate sensory signals. Nerves may be stimulated by surgically implanting electrodes in, around or near the nerves and driving the electrodes from an implanted or external source of electricity.

The phrenic nerve normally causes the contractions of the diaphragm that are necessary for breathing. Various conditions can prevent appropriate signals from being delivered to the phrenic nerve. These include:
chronic or acute injury to the spinal cord or brain stem;
Amyotrophic Lateral Sclerosis (ALS);
disease affecting the spinal cord or brain stem; and,
decreased day or night ventilatory drive (e.g. central sleep apnea, Ondine's curse).
These conditions affect significant numbers of people.

Mechanical ventilation may be used to help patients breathe. Some patients require chronic mechanical ventilation. Mechanical ventilation can be lifesaving but has a range of significant problems. Mechanical ventilation:
tends to provide insufficient venting of the lungs. This can lead to accumulation of fluid in the lungs and susceptibility to infection.
requires apparatus that is not readily portable. A patient on ventilation is tied to a ventilator. This can lead to atrophy of muscles (including breathing muscles) and an overall decline in well being.
can adversely affect venous return because the lungs are pressurized.
interferes with eating and speaking.
requires costly maintenance and disposables.

Phrenic nerve pacing uses electrodes implanted in the chest to directly stimulate the phrenic nerve. The Mark IV Breathing Pacemaker System available from Avery Biomedical Devices, Inc. of Commack, N.Y. USA is a diaphragmatic or phrenic nerve stimulator that consists of surgically implanted receivers and electrodes mated to an external transmitter by antennas worn over the implanted receivers. Implanting electrodes and other implantable components for phrenic nerve pacing requires significant surgery. The surgery is complicated by the fact that the phrenic nerve is small (approx. diameter 2 mm) and delicate. The surgery involves significant cost.

Laproscopic diaphragm pacing being developed by Case Western Reserve University bio-medical engineers and physician researchers is another technique for controlling breathing. Devices for use in Laproscopic diaphragm pacing are being developed by Synapse Biomedical, Inc. Laproscopic diaphragm pacing involves placing electrodes at motor points of the diaphragm. A laparoscope and a specially designed mapping procedure are used to locate the motor points.

References that in the field of nerve stimulation include:
Moffitt et al., WO 06/110338A1, entitled: TRANSVASCULAR NEURAL STIMULATION DEVICE;
Caparso et al., US 2006/0259107, entitled: SYSTEM FOR SELECTIVE ACTIVATION OF A NERVE TRUNK USING A TRANSVASCULAR RESHAPING LEAD;
Dahl et al., WO 94/07564 entitled: STENT-TYPE DEFIBRILLATION ELECTRODE STRUCTURES;
Scherlag et al., WO 99/65561 entitled: METHOD AND APPARATUS FOR TRANSVASCULAR TREATMENT OF TACHYCARDIA AND FIBRILLATION;
Bulkes et al., US20070288076A1 entitled: BIOLOGICAL TISSUE STIMULATOR WITH FLEXIBLE ELECTRODE CARRIER;
Weinberg et al., EP 1304135 A2 entitled: IMPLANTABLE LEAD AND METHOD FOR STIMULATING THE VAGUS NERVE;
Moffitt et al., US20060259107 entitled: SYSTEM FOR SELECTIVE ACTIVATION OF A NERVE TRUNK USING A TRANSVASCULAR RESHAPING LEAD;
Denker et al. U.S. Pat. No. 6,907,285 entitled: IMPLANTABLE DEFIBRILLATOR WITH WIRELESS VASCULAR STENT ELECTRODES;
Chavan et al. US20070093875 entitled IMPLANTABLE AND RECHARGEABLE NEURAL STIMULATOR;
Rezai, U.S. Pat. No. 6,885,888 entitled ELECTRICAL STIMULATION OF THE SYMPATHETIC NERVE CHAIN;
Mehra, U.S. Pat. No. 5,170,802 entitled IMPLANTABLE ELECTRODE FOR LOCATION WITHIN A BLOOD VESSEL;
Mahchek et al. U.S. Pat. No. 5,954,761 entitled: IMPLANTABLE ENDOCARDIAL LEAD ASSEMBLY HAVING A STENT;
Webster Jr. et al. U.S. Pat. No. 6,292,695 entitled: METHOD AND APPARATUS FOR TRANSVASCULAR TREATMENT OF TACHYCARDIA AND FIBRILLATION;
Stokes, U.S. Pat. No. 4,643,201;
Ela Medical SA, EP 0993840A, U.S. Pat. No. 6,385,492
WO 9407564 describes stent-type electrodes that can be inserted through a patient's vasculature.
WO 9964105A1 describes transvascular treatment of tachycarida.

WO 9965561A1 describes a method and apparatus for transvascular treatment of tachycardia and fibrillation.

WO02058785A1 entitled VASCULAR SLEEVE FOR INTRAVASCULAR NERVE STIMULATION AND LIQUID INFUSION describes a sleeve that includes an electrode for stimulating nerves.

WO 06115877A1 describes vagal nerve stimulation using vascular implanted devices.

WO 07053508A1 entitled INTRAVASCULAR ELECTRONICS CARRIER AND ELECTRODE FOR A TRANSVASCULAR TISSUE STIMULATION SYSTEM and US20070106357A1 describe an intravascular mesh type electrode carrier in which the conductor of a lead is interwoven into the carrier mesh.

U.S. Pat. No. 5,224,491 describes implantable electrodes for use in blood vessels.

U.S. Pat. No. 5,954,761 describes an implantable lead carrying a stent that can be inserted into the coronary sinus.

U.S. Pat. No. 6,006,134 describes transvenous stimulation of nerves during open heart surgery.

U.S. Pat. No. 6,136,021 describes an expandable electrode for coronary venous leads (the electrode can be placed or retained in the vasculature of the heart).

Spreigl et al. U.S. Pat. No. 6,161,029 entitled: APPARATUS AND METHOD FOR FIXING ELECTRODES IN A BLOOD VESSEL describes fixing electrodes in blood vessels.

U.S. Pat. No. 6,438,427 describes electrodes for insertion into the coronary sinus.

U.S. Pat. No. 6,584,362 describes leads for pacing and/or sensing the heart from within the coronary veins.

U.S. Pat. No. 6,778,854 describes use of electrodes in the Jugular vein for stimulation of the Vagus nerve.

U.S. Pat. No. 6,934,583 discloses stimulation of the Vagus nerve with an electrode in a blood vessel.

U.S. Pat. No. 7,072,720 describes catheter and tube electrode devices that incorporate expanding electrodes intended to contact the interior walls of blood vessels or anatomic structures in which the electrode devices are implanted as well as methods involving stimulation of the vagus nerve.

U.S. Pat. No. 7,184,829 discloses transvascular stimulation of a vagal nerve.

U.S. Pat. No. 7,225,019 discloses intravascular nerve stimulation electrodes that may be used in the Jugular vein.

U.S. Pat. No. 7,231,260 describes intravascular electrodes.

Schauerte et al., US 2002/0026228 entitled: ELECTRODE FOR INTRAVASCULAR STIMULATION, CARDIOVERSION AND/OR DEFIBRILLATION;

Jonkman et al., U.S. Pat. No. 6,006,134

Bonner et al., U.S. Pat. No. 6,201,994

Brownlee et al., U.S. Pat. No. 6,157,862

Scheiner et al., U.S. Pat. No. 6,584,362

Psukas, WO 01/00273

FR 2801509, US 2002065544

Morgan, U.S. Pat. No. 6,295,475

Bulkes et al., U.S. Pat. No. 6,445,953

Rasor et al. U.S. Pat. No. 3,835,864 entitled: INTRA-CARDIAC STIMULATOR

Denker et al. US20050187584

Denker et al. US20060074449A1 entitled: INTRAVASCULAR STIMULATION SYSTEM WITH WIRELESS POWER SUPPLY;

Denker et al. US20070106357A1 entitled: INTRAVASCULAR ELECTRONICS CARRIER ELECTRODE FOR A TRANSVASCULAR TISSUE STIMULATION SYSTEM;

Boveja et al. US20050143787

*Transvenous Parassympathetic cardiac nerve stimulation; an approach for stable sinus rate control*, Journal of Cardiovascular Electrophysiology 10(11) pp. 1517-1524 November 1999

*Transvenous Parassympathetic nerve stimulation in the inferior vena cava and atrioventricular conduction*, Journal of Cardiovascular Electrophysiology 11(1) pp. 64-69, January 2000.

Planas et al., *Diaphragmatic pressures: transvenous vs. direct phrenic nerve stimulation*, J. Appl. Physiol. 59(1): 269-273, 1985.

Yelena Nabutovsky, M. S. et al., *Lead Design and Initial Applications of a New Lead for Long-Term Endovascular Vagal Stimulation*, PACE vol. 30, Supplement 1, January 2007 p. S215

Other references of interest include:

Amundson, U.S. Pat. No. 5,779,732

There remains a need for surgically simpler, cost-effective and practical apparatus and methods for nerve stimulation.

SUMMARY OF THE INVENTION

This invention has a range of aspects. One aspect of the invention provides electrodes for transvascular stimulation of nerves. In embodiments, electrode structures comprise at least one electrode supported on an electrically-insulating backing sheet; and, a structure for holding the backing sheet against the inner wall of a blood vessel with the electrode in contact with the inner wall of the blood vessel. In some embodiments, the backing sheet is designed to unroll inside the lumen of a blood vessel to fit around the periphery of the lumen of a blood vessel. In such embodiments, the backing sheet can comprise the structure for holding the backing sheet against the inner wall of the blood vessel. In other embodiments an expandable stent or a tube is provided to hold the backing sheet and electrodes against the blood vessel wall.

Another aspect of the invention comprises a nerve stimulation system comprising a stimulation signal generator and first and second electrode structures. The first electrode structure comprises a first plurality of electrodes and is dimensioned to be implantable at a position along a lumen of a person's left subclavian vein that is proximate to the left phrenic nerve. The second electrode structure comprises a second plurality of electrodes and is dimensioned to be implantable at a position along a lumen of the person's superior vena cava that is proximate to the right phrenic nerve. The system comprises means such as electrical leads, a wireless system or the like for transmitting signals from the signal generator to the first and second pluralities of electrodes.

Another aspect of the invention provides a method for regulating breathing of a person. The method comprises implanting at least one of: a first electrode structure at a position along a lumen of the left subclavian vein that is proximate to the left phrenic nerve; and a second electrode structure at a position along a lumen of the superior vena cava that is proximate to the right phrenic nerve; and subsequently stimulating the left- and right-phrenic nerves by applying stimulation signals to electrodes of the first and second electrode structures.

Further aspects of the invention and features of specific example embodiments of the invention are described below.

BRIEF DESCRIPTION OF THE DRAWINGS

The accompanying drawings illustrate non-limiting example embodiments of the invention.

FIG. 1 shows a number of nerves adjacent to a blood vessel.

FIG. 2 is a schematic diagram of a transvascular nerve stimulation apparatus according to an example embodiment.

DESCRIPTION

Figure 3:
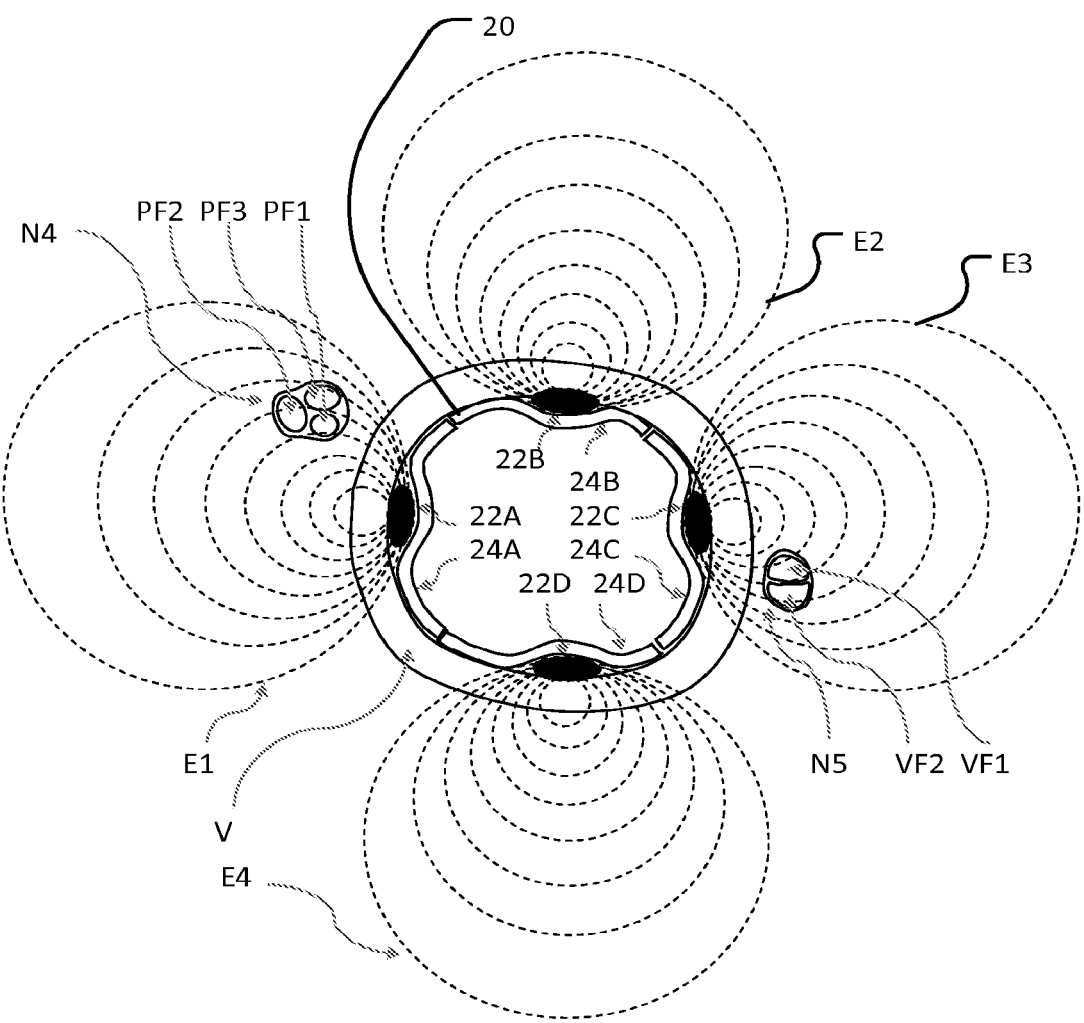
FIG. 3 is a cross section through an electrode structure having multiple electrodes or rows of electrodes spaced apart around an inner wall of a blood vessel.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

This invention relates to transvascular stimulation of nerves. In transvascular stimulation, suitable arrangements of one or more electrodes are positioned in a blood vessel that passes close to a nerve to be stimulated. Electrical currents pass from the electrodes through a wall of the blood vessel to stimulate the nerve.

FIG. 1 shows three nerves, N1, N2 and N3 that pass nearby a blood vessel V having a wall W defining a lumen L. FIG. 1 is illustrative and not intended to represent any specific blood vessel or nerves. FIG. 1 represents any suitable one of the various places in the body where nerves pass nearby to veins or arteries. Nerves N1 and N2 extend roughly parallel to blood vessel V and nerve N3 extends generally transversely to blood vessel V, at least in their parts depicted in FIG. 1. Nerve N1 is closer to blood vessel V than nerve N2.

FIG. 2 illustrates schematically the use of an electrode structure 10 inserted into lumen L of blood vessel V to stimulate nerve N1. Electrode structure 10 comprises an electrode 12, an electrically-insulating backing layer 14 and a means 15 for holding electrode 12 and backing layer 14 in place against the inner wall of blood vessel V. Electrode 12 may be attached to backing layer 14. This is not mandatory, however. It is sufficient that electrode 12 can be held against or at least in close proximity to the wall W of the blood vessel and that backing layer 14 covers the side of electrode 12 facing into lumen L. Various example structures that may be used as means 15 are described below. Electrode structures which provide electrodes backed by electrically-insulating barriers as illustrated generally in FIG. 2 may be provided in a variety of ways.

Electrode 12 is connected to a signal generator 18 by a suitable lead 17. Signal generator 18 supplies electrical current to electrode 12 by way of lead 17. Signal generator 18 may be implanted or external to the body. Signal generator 18 may, for example, comprise an implantable pulse generator (IPG).

In some embodiments electrode structure 10 includes a circuit (not shown) for applying signals to one or more electrodes 12 and a battery, system for receiving power wirelessly or another supply of electrical power. In such embodiments, signal generator 18 may deliver control signals which cause the circuit to apply stimulation signals to electrode 12 by way of a suitable wireless link technology. The wireless link may provide communication of the control signals between a small transmitter associated with signal generator 18 and a small receiver associated with electrode structure 10. With suitably miniature circuitry, it may be possible to provide a signal generator 18 that is co-located in a sufficiently large blood vessel with electrode structure 10. The signal generator 18 may, for example, comprise a thin electronic circuit embedded within backing sheet 14.

Electrode 12 serves as a source or as a sink for electrical current. Depending upon the nature of the electrical signals generated by signal generator 18 electrode 12 may serve as a current source at some times and as a current sink at other times. Another electrode or group of electrodes (not shown in FIG. 2) in contact with the patient serves to complete an electrical circuit. The other electrode or group of electrodes may be incorporated in electrode structure 10 (as is usually preferable) or may be separate.

Electrically-insulating backing layer 14 presents a high-impedance to the flow of electrical current and therefore reduces the amount of current flow through the blood in blood vessel V. It is not mandatory that layer 14 have an extremely high electrical resistance. It is sufficient if layer 14 has a resistance to the flow of electricity through layer 14 that is significantly greater than that presented by the blood in blood vessel V. Blood typically has a resistivity of about 120 to 190 Ωcm. In example embodiments, the blood in a blood vessel may provide an electrical resistance between closely-spaced electrical contacts that is inversely proportional to the dimensions of the lumen of the blood vessel. In large blood vessels the longitudinal electrical resistance between reasonable closely-spaced contacts can be a few tens of ohms for example. Layer 14 preferably provides an electrical resistance of at least a few hundred ohms, preferably a few kilo ohms or more to the flow of electrical current through the thickness of layer 14. Layer 14 could have electrically conductive members such as leads and the like embedded within it or electrically-conductive on its inner surface and still be considered to be 'electrically-insulating'.

By making layer 14 of a suitable material such as silicone rubber elastomer, a biocompatible plastic, or another biocompatible insulating material it is easily possible to provide a backing layer 14 having a suitable resistance to the flow of electrical current. FIG. 2 illustrates how the presence of backing layer 14 directs the electric field E (illustrated schematically in FIG. 2 by lines of equipotential) outwardly from blood vessel V.

In FIG. 2, the delivery of electrical stimulation to nerve N1 is enhanced by:

- Locating electrode 12 against the internal wall of blood vessel V at a location close to nerve N1;
- Providing an electrode 12 having a relatively large contact surface that can achieve a large contact area with the inner wall of blood vessel V;
- Curving the contact surface of electrode 12 to roughly match the curvature of the inner face of blood vessel V;
- Providing electrically-insulating backing sheet 14.

With these features, a significantly lower stimulation intensity is required to stimulate target nerve N1 than would be the case for wire electrodes located in lumen L in contact with the blood in lumen L. Additionally, selectivity for a nerve of interest is improved. Advantageously, electrodes 12 have active surface areas in the range of about ½ mm$^2$ to about 5 mm$^2$. In some embodiments, each electrode has an active surface area on the order of 2 mm$^2$.

Electrode structure 10 may be introduced into blood vessel V in a minimally-invasive, safe way. Blood vessel V may be a relatively large blood vessel that courses in the vicinity of the target nerve N1. In some embodiments, electrode structure 10 comprises a flexible multi-contact electrode carrier sheet (ECS) of suitable dimensions. The sheet may be tightly coiled prior to its insertion into blood vessel V. Once within blood vessel V the sheet may be allowed to unwind so as to bring electrode 12 into contact with wall W of blood vessel V.

An electrode structure may support multiple electrodes. FIG. 3 shows an example electrode structure 20 which supports a number of electrodes including electrodes 22A, 22B, 22C and 22D (collectively electrodes 22). Other electrodes out of the plane of FIG. 3 may also be present. In the illustrated embodiment, electrodes 22A, 22B, 22C and 22D are circumferentially spaced approximately equally around the perimeter of the inside wall of blood vessel V. Each electrode 22 is insulated from the lumen of blood vessel V by a thin flexible insulating sheet 24 (individually identified as 24A, 24B, 24C and 24D. Each of the insulating sheets 24 is conformally disposed against the internal wall of blood vessel V. In alternative embodiments, two or more electrodes are disposed on a common insulating sheet. Insulating sheets 24 may be joined together or may be different parts of a continuous sheet.

E1, E2, E3 and E4 illustrate the areas corresponding to electrodes 24A through 24D in which the electrical field associated with current flow at the corresponding electrode is strong enough to stimulate a nerve. Increasing the strength of the signal (e.g. a stimulation pulse) at an electrode increases the affected area (as indicated by the larger dotted regions).

FIG. 3 shows two nerves N4 and N5. It can be seen that a stimulation signal from electrode 22A can stimulate nerve N4. A stimulation signal from electrode 22B can stimulate nerve N5. The arrangement of blood vessel V and nerves N4 and N5 is like the arrangement of the internal jugular vein and the phrenic and vagus nerves in the neck region of a person. With an arrangement as shown in FIG. 3, a target phrenic nerve at the location of N4 can be preferentially stimulated by electrode 22A due to greater proximity of electrode 22A and also due to the shape of the area E1 affected by electrode 22A. The vagus nerve at location N5 is usually approximately diametrically opposite from electrode 22A and is not affected by signals delivered at normal levels at electrode 22A. The vagus nerve is, however, affected by signals delivered at electrode 22C.

The phrenic nerve and vagus nerve in adult humans are each typically about 2 mm in diameter. The lumen of the internal jugular vein in adult humans is typically in the range of about 10 mm to 20 mm in diameter. The distance from the phrenic nerve to the internal jugular vein and the distance from the vagus nerve to the internal jugular vein are each typically in the range of about 2 mm to about 10 mm. Generally the phrenic nerve and vagus nerve are on opposite sides of the internal jugular vein so that they are roughly 15 mm to 30 mm apart from one another. This arrangement facilitates the ability to perform transvascular stimulation of only the vagus nerve or only the phrenic nerve without stimulating the other nerve. A system according to some embodiments stimulates the phrenic nerve or vagus nerve only. A system according to other embodiments selectively stimulates either or both of the phrenic and vagus nerves from an electrode structure located in the internal jugular vein.

In many cases, nerves comprise a plurality of fascicles. For example, in the example illustrated in FIG. 3, the phrenic nerve N4 is composed of three phrenic fascicles PF1, PF2, and PF3. These phrenic fascicles may be selectively recruited by progressive levels of stimulation current at electrode 22A. At lower stimulation levels, only PF1 is recruited. At higher levels PF1 and PF2 are both recruited. At still higher levels, all of PF1, PF2 and PF3 are recruited. In FIG. 3, the vagus nerve N5 is composed of two vagus fascicles VF1, and VF2 that may be selectively recruited by progressive levels of stimulation current at electrode 22C. At lower stimulation levels only VF1 is recruited. At higher stimulation levels both VF1 and VF2 are recruited.

It is desirable that an electrode structure provide a minimum obstruction to the flow of blood in lumen L of a blood vessel V. Therefore, electrode structures are preferably thin in comparison to the inner diameter of blood vessel V. In some embodiments, a structure that supports electrodes and insulating backing sheets gently urges the electrodes and insulating backing sheets radially outward in lumen L so as to leave an open passage for blood flow past the electrode structure. To prevent the disruption or blockage of blood flow in a blood vessel, the cross-sectional area of an intravascular electrode structure should not exceed a certain fraction of the cross-sectional area of the lumen of the blood vessel. A round blood vessel with an internal diameter of 10 mm has a cross-sectional area of approximately 75 mm$^2$. The circumference of the electrode structure when expanded in the blood vessel should preferably not be greater than about 10×πmm, (approximately 30 mm). If the thickness of an electrode structure is between about 0.3 and 0.5 mm then the cross-sectional area of the electrode structure will be about 10 mm$^2$ to 15 mm$^2$, which represents less than 20% of the lumen of the vessel.

Figure 4A:
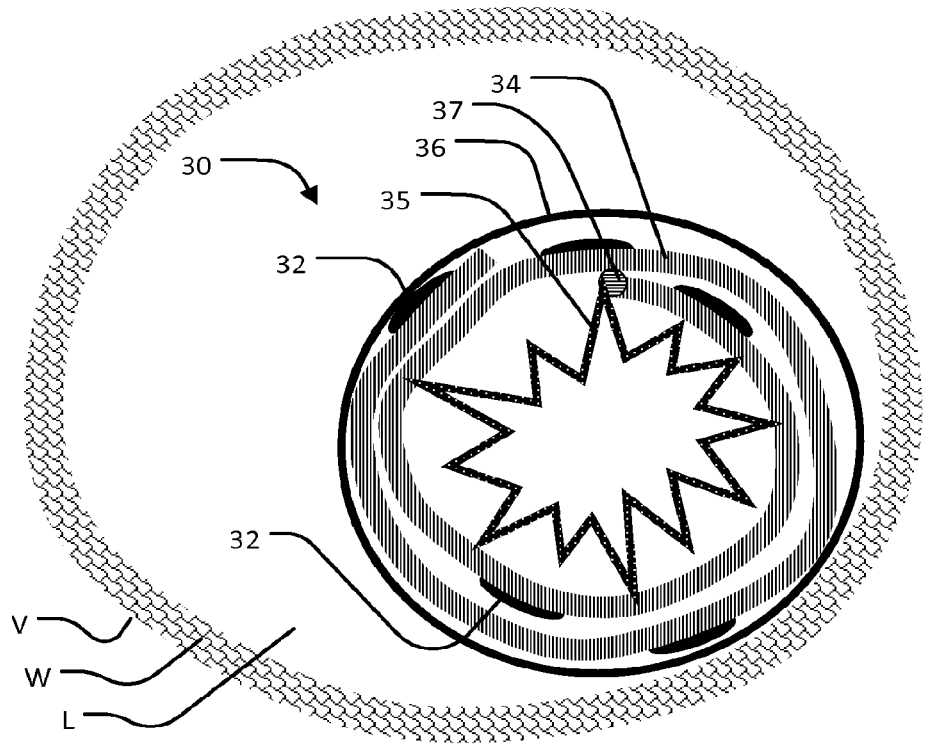
FIGS. 4A, 4B and 4C are partially schematic cross sectional views illustrating stages in the implanting of an electrode structure according to an example embodiment which includes an expandable stent in a blood vessel.
Figure 4B:
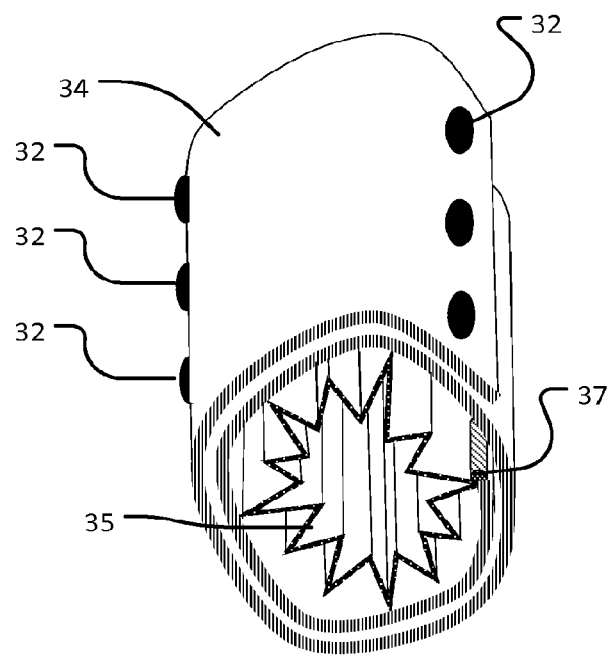
Figure 4C:
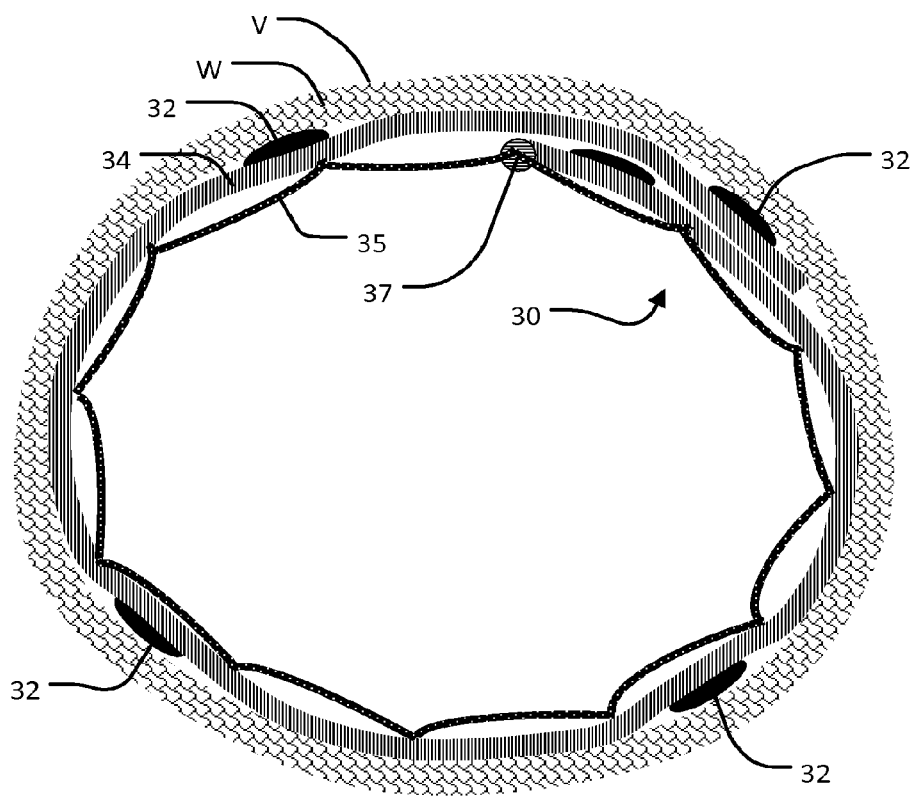

FIGS. 4A, 4B and 4C show an electrode structure 30 according to an example embodiment. Electrode structure 30 comprises a plurality of electrodes 32 disposed on a flexible electrically-insulating sheet 34. Electrode structure is initially introduced into a blood vessel V tightly curled up around an expandable stent 35 inside an introducer tube 36. Stent 35 may, for example, comprise an expandable wire stent. A variety of suitable expandable wire stents is available from medical devices manufacturers.

Electrode structure 30 is guided to a desired location in a blood vessel V inside introducer tube 36. At the desired location, introducer tube 36 is retracted to allow electrically-insulating sheet 34 to begin to unroll as shown in FIG. 4B. Stent 35 is then expanded in order to further unroll electrically-insulating sheet 34 and to urge electrically insulating sheet 34 and the electrodes 32 carried on electrically-insulating sheet 34 against the inner wall of blood vessel V as shown in FIG. 4C.

In the illustrated embodiment, stent 35 is attached to sheet 34 at a point, row of points or line 37. Stent 35 is left in place to retain electrodes 32 and sheet 34.

Stent 35 may comprise any suitable type of expandable stent. A wide range of such stents are known. Stent 35 is expanded in a manner appropriate to the stent. For example, in some embodiments a balloon is placed inside the stent and the stent is expanded by inflating the balloon. The balloon may be withdrawn after the stent has been expanded.

Figure 5A:
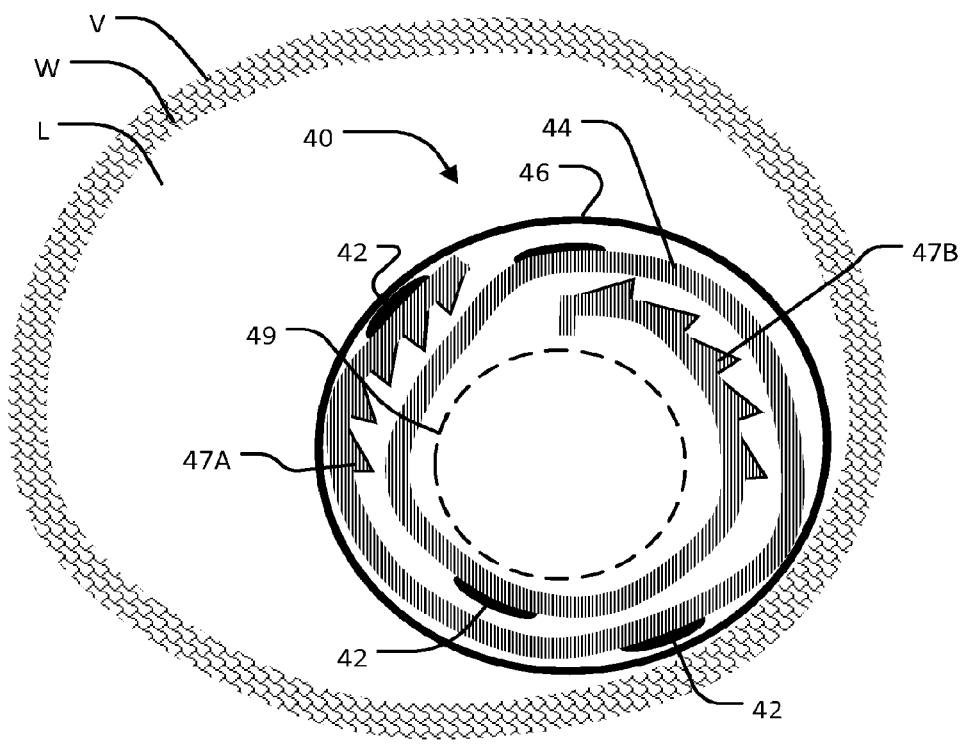
FIGS. 5A, 5B and 5C are partially schematic cross sectional views illustrating an electrode structure according to an embodiment having an engagement structure for holding the electrode structure expanded against an inner wall of a blood vessel.
Figure 5B:
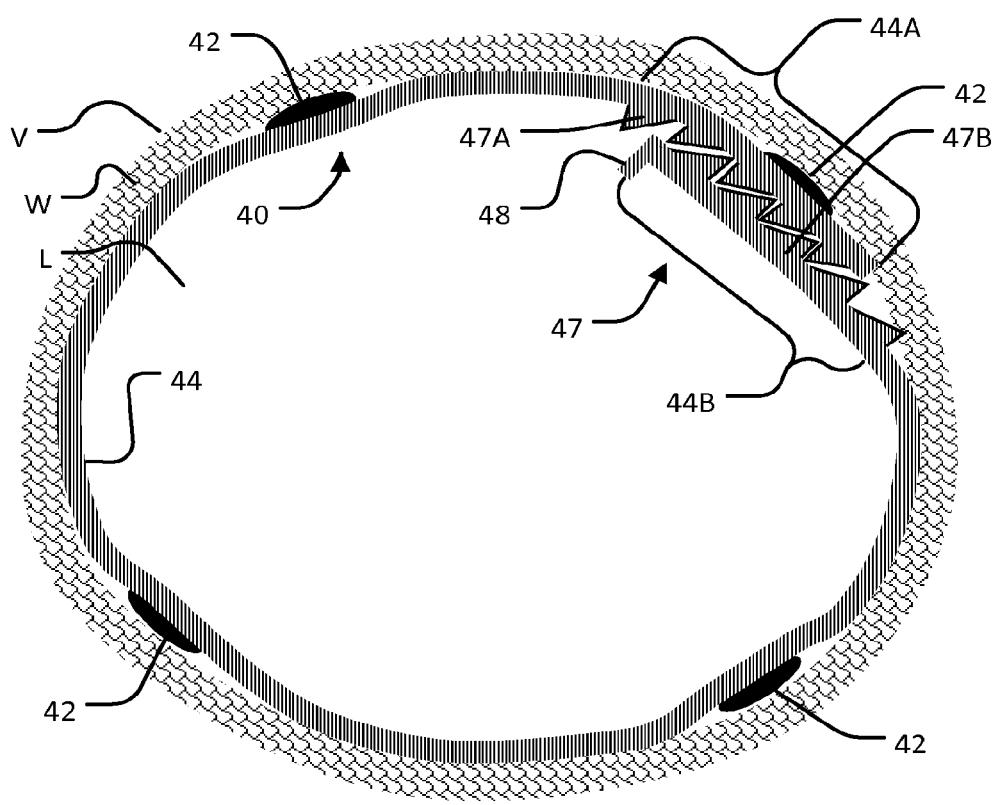
Figure 5C:
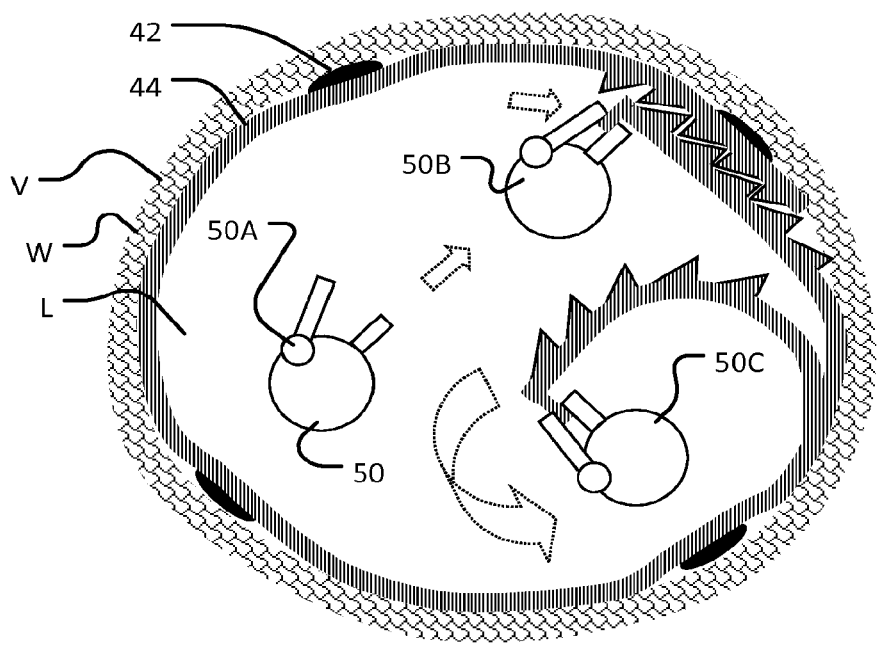

FIGS. 5A, 5B and 5C illustrate an electrode structure 40 which is similar to electrode structure 30 except that it has electrodes 42 supported on a flexible sheet 44 and an engagement mechanism 47 which allows opposed edges portions 44A and 44B of flexible sheet 44 to be locked together when flexible sheet 44 has been opened within the lumen L of blood vessel V. The locking together of edge portions 44A and 44B holds flexible sheet 44 in an expanded configuration with electrodes 42 contacting the inner surface of wall W. Electrode structure 40 does not have a stent inside flexible sheet 44 (although a stent could optionally be added to provide further support for sheet 44). Sheet 44 may be made so that it has a tendency to unroll toward a configuration that is less tightly-rolled than shown in either of FIG. 5A or 5B. This tendency will bias sheet 44 to open into the configuration of FIG. 5B when removed from insertion tube 46 and will help to hold sheet 44 in place inside blood vessel V.

In the illustrated embodiment, mechanism 47 comprises mating sets of ridges 47A and 47B that extend longitudinally respectively along edge portions 44A and 44B. Ridges 47A and 47B are on opposing major surfaces of sheet 44 so that they can contact one another when sheet 44 is sufficiently unrolled. As shown in FIG. 5B, ridges 47A and 47B interlock when sheet 44 is unrolled as fully as the dimension of blood vessel V will permit. Mechanism 47 thus serves to retain sheet 44 and electrodes 42 snugly against the inside of wall W and prevent sheet 44 from curling inwardly or moving away from the wall W.

In preferred embodiments, mechanism 47 permits engagement of edge portions 44A and 44B in a range of degrees of overlap. Thus, mechanism 47 allows engagement of edge portions 44A and 44B when sheet 44 has been expanded against the inner wall of blood vessels having sizes within a given range of different sizes.

Alternative engagement mechanisms 47 are possible. For example, in some embodiments, a biocompatible adhesive is introduced between edge portions 44A and 44B. In other embodiments, ridges or other interlocking features and a biocompatible glue are both used.

An electrode structure 40 may be placed in a desired location by: introducing and sliding the electrode structure along a blood vessel to a desired location; at the desired location, sliding electrode structure 40 out of tube 46; if electrode structure 40 is partially or entirely self-unwinding, allowing electrode structure 40 to unwind; and, if necessary, inflating a balloon 49 to fully expand electrode structure 40 and/or engage engagement mechanism 47. Introducing the electrode structure may comprise cannulating the blood vessel and introducing the electrode structure at the cannulation site.

FIG. 5C illustrates a method for removing or relocating an electrode structure 40. Electrode structure 40 comprises a tab 48 or other projection that is attached to sheet 44 near or at an inside edge thereof and is graspable from within lumen L. A tool 50 is inserted into lumen L and has jaws 51 operable to grasp tab 48. At position 50A jaws 51 of tool 50 are opened to receive tab 48. At position 50B, jaws 51 have been operated to grasp tab 48. At position 50C tool 50 has been moved toward the center of lumen L and tool 50 has thereby peeled the inner edge of sheet 44 away from wall W. Tool 50 may be rotated about its axis to roll electrode structure 40 into a smaller configuration. Electrode structure 40 may then be moved along blood vessel 44 to a new position; or pulled into an insertion tube for safe removal from blood vessel V.

Figure 6:
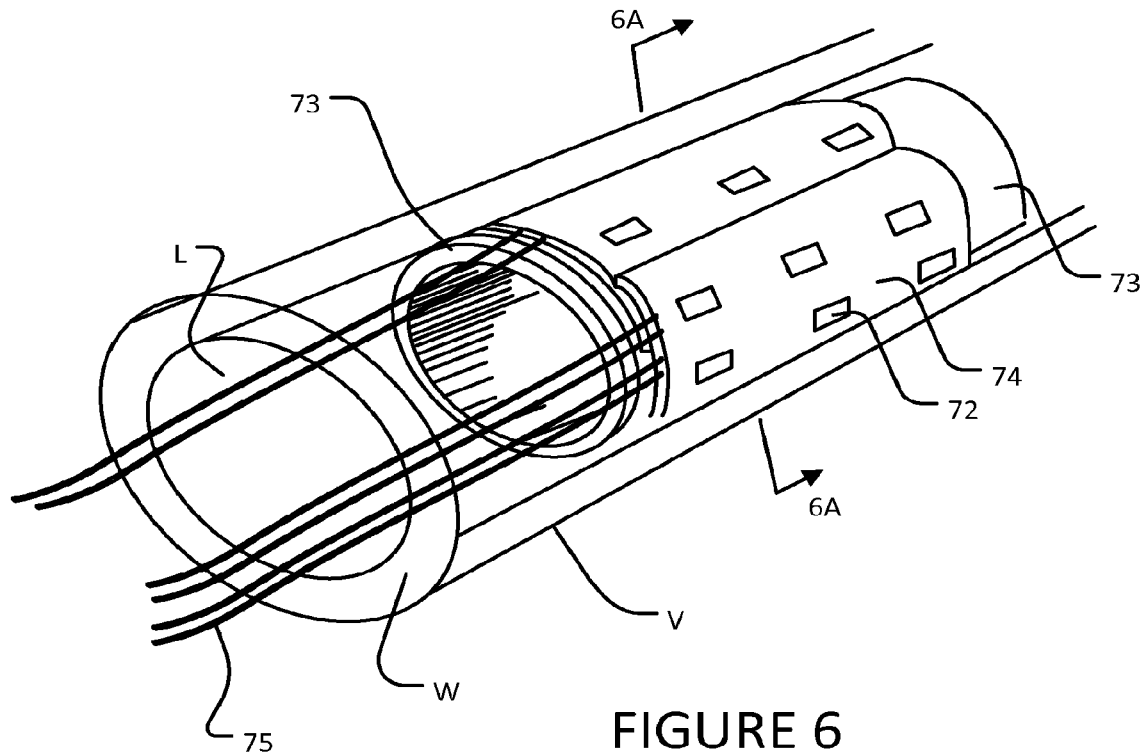
FIGS. 6 and 6A are respectively perspective and cross sectional views showing an electrode structure according to another embodiment wherein electrodes are held against an inner wall of a blood vessel by a retention tube.
Figure 6A:
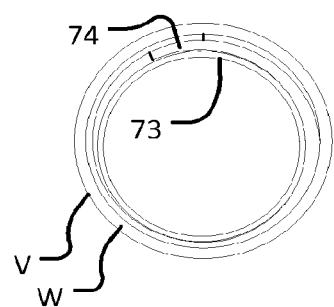

FIGS. 6 and 6A show an electrode structure 70 that includes a rolled, flexible electrically-insulating sheet 74 carrying electrodes 72. Sheet 74 may be opened by partial unrolling within a blood vessel V. A tubular retainer 73 may then be inserted to retain sheet 74 and electrodes 72 in place against a wall of the blood vessel. In cases where electrode structure 70 is to be inserted into the blood vessel through an incision that is smaller than the lumen of the blood vessel then tubular retainer 73 may be expandable so that it can be introduced through the opening and then expanded to a size suitable for retaining sheet 74 and electrodes 72.

Retainer 73 has a diameter selected such that, when placed inside sheet 74, it will retain sheet 74 and electrodes 72 in close apposition to the inside wall of the blood vessel for as long as required. The outside diameter of retainer 73 is chosen to closely match the inner diameter of the blood vessel V minus twice the thickness of sheet 74. For example, for a blood vessel with an inside diameter of 10 mm and an electrode structure 70 with sheet thickness of ½ mm, the outside diameter of retainer 73 should be approximately 10 mm−2×½ mm=9 mm. Retainers 73 in a range of diameters may be provided to allow a surgeon to select and insert the best size. In typical blood vessels having inner diameters of 10 mm or more, the length of retainer 73 should be at least about twice its diameter to ensure that retainer 73 will not tilt inside the blood vessel. The wall thickness of retainer 73 may be fairly small, for example, up to about 0.3 mm or so. Retainer 73 may be made of a suitable material such as a biocompatible metal (e.g. stainless steel or titanium) or a high-strength biocompatible polymer.

Wires 75 carry signals from a signal generator to electrodes 72. In an alternative embodiment, a signal generator is integrated with electrode structure 70. Such as signal generator may be controlled to issue stimulation pulses in response to control signals provided by way of a suitable wireless link.

FIGS. 7A to 7G show examples of electrode structures. Electrode structure 80 of FIG. 7A has four electrodes 82 (individually 82A to 82D) supported on a major face 81 of a flexible insulating sheet 84. Insulated leads 85 connect electrodes 82 to a signal generator (not shown in FIG. 7A). Sheet 84 may comprise a flexible layer of silicone for example. Electrodes 82 and electrode leads 85 may be of any suitable shape and material; e.g., stainless steel or platinum-iridium multi-stranded wire electrodes with Teflon™ coated wire leads.

An electrode structure 80 may be fabricated, for example, by connecting suitable electrodes to coated wire leads and then embedding the electrodes and leads in a layer of silicone such that the electrodes are exposed on one major face of the silicone layer but not the other.

Electrode structure 80 may be used to stimulate nerves by inserting electrode structure 80 into a blood vessel with electrodes 82 facing outwardly; and connecting any one electrode to the negative output of a standard constant-current (preferably) or constant-voltage nerve stimulator (cathodic stimulation) with respect to a remote reference electrode. Alternatively, any two electrodes 82 can be selected as anode and cathode.

Electrode structure 80 is similar to a nerve cuff but 'inside out'. Each electrode preferentially stimulates a sector of tissue that radiates outwardly from a blood vessel V and spans a limited angle. For example, in an electrode structure having four electrodes disposed approximately every 90 degrees around the circumference of a blood vessel, the volume of tissue affected by each electrode may span approximately 90 degrees (see FIG. 3 for example).

A further improvement in angular selectivity may be obtained by providing longitudinal ridges on the outer major surface of electrode structure 80. The ridges enhance the electrical separation between circumferentially-adjacent electrodes 82. The ridges may be similar to the ridges described in Hoffer et al. U.S. Pat. No. 5,824,027 entitled NERVE CUFF HAVING ONE OR MORE ISOLATED CHAMBERS which is hereby incorporated herein by reference. Ridges 86 are shown schematically in FIG. 7A.

Optionally, sheet 84 may include geometrical complexities such as holes or protuberances to provide a better substrate for connective tissue adhesion and so increase the long-term mechanical stability and immobility of structure 80 inside a blood vessel.

Figure 7A:
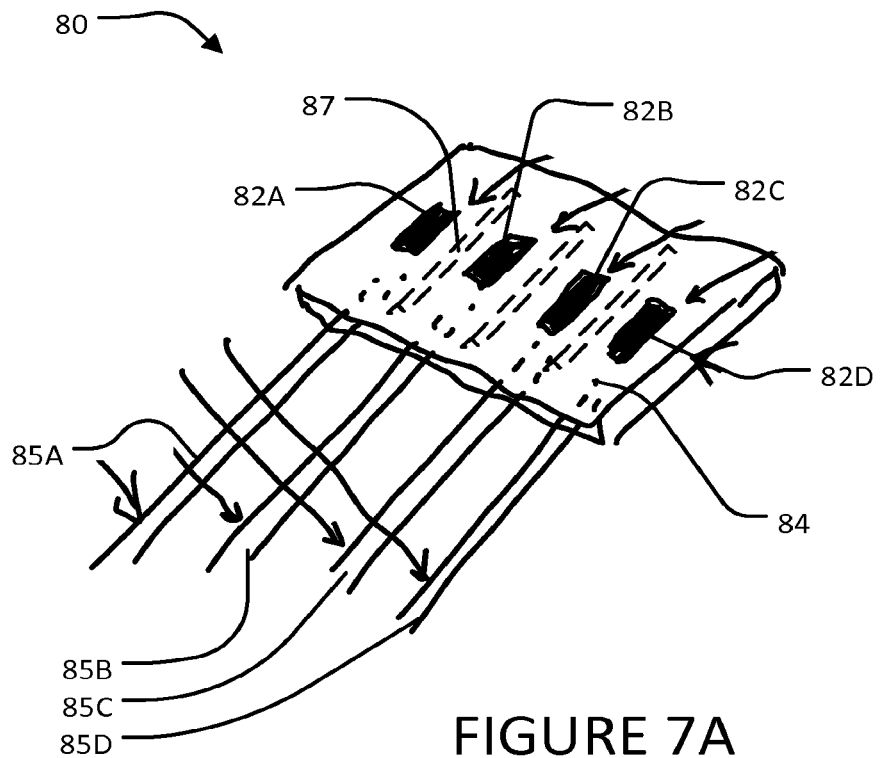
FIGS. 7A and 7B are perspective views showing an electrode structure having four electrodes respectively in a flat configuration and a rolled configuration. In the rolled configuration, the electrodes face radially outward.
Figure 7B:
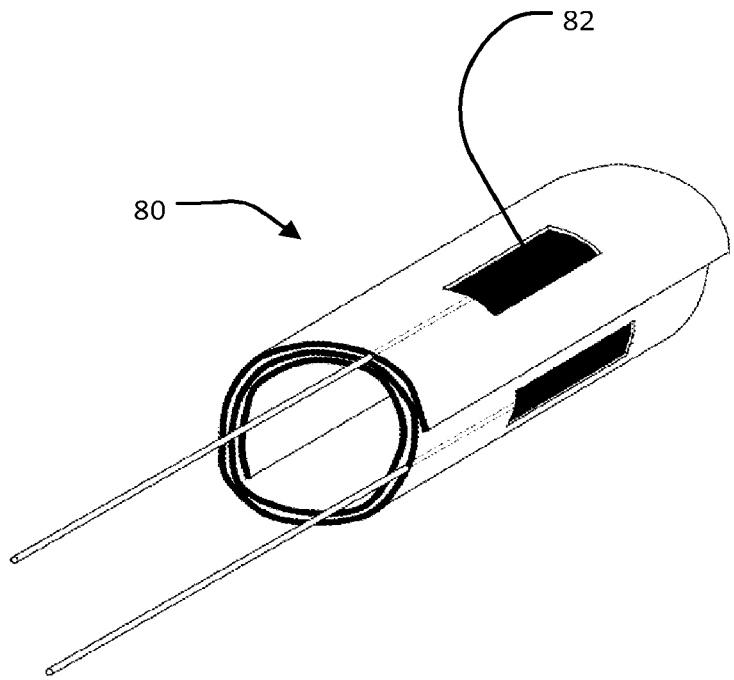

FIG. 7B shows an electrode structure like electrode structure 80 wrapped into a tight spiral with electrodes facing out in preparation for insertion into a blood vessel.

Figure 7C:
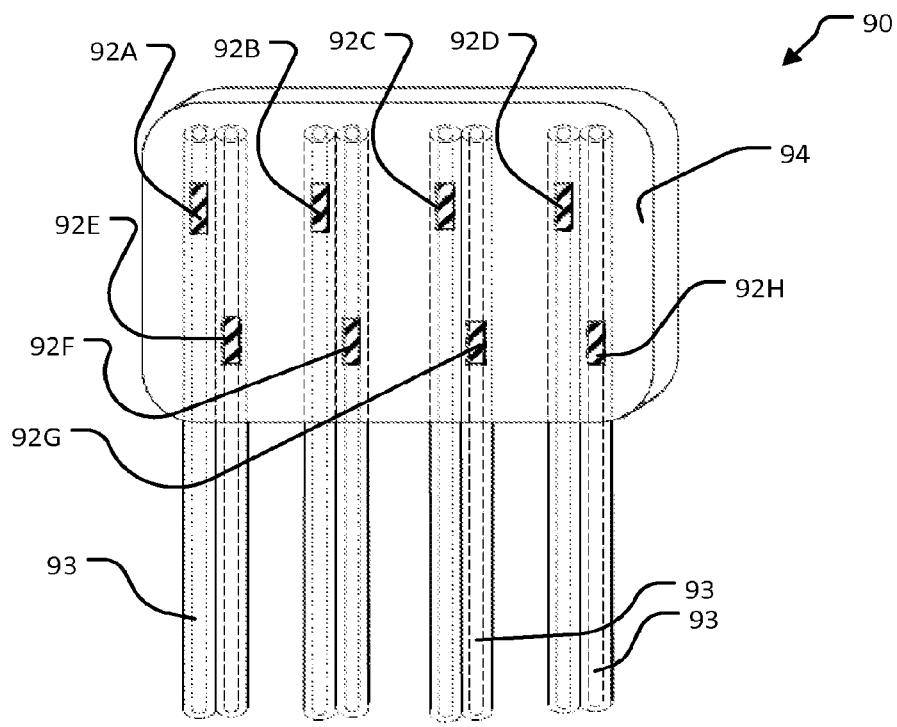
FIGS. 7C and 7F are views showing plan views of unrolled electrode structures having electrodes that may be used in bipolar pairs (among other electrical configurations).
Figure 7D:
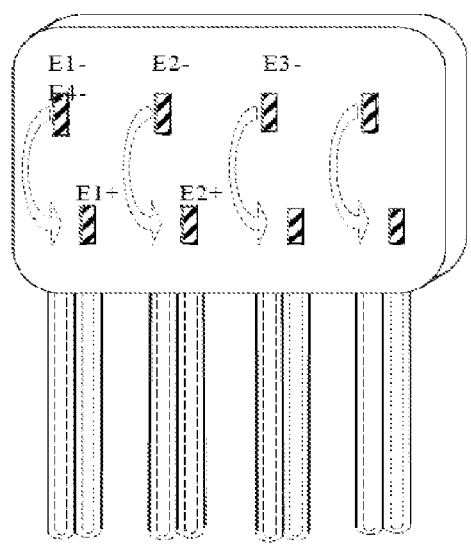
FIGS. 7D and 7E show example ways for pairing the electrodes of the electrode structure of FIG. 7C.
Figure 7E:
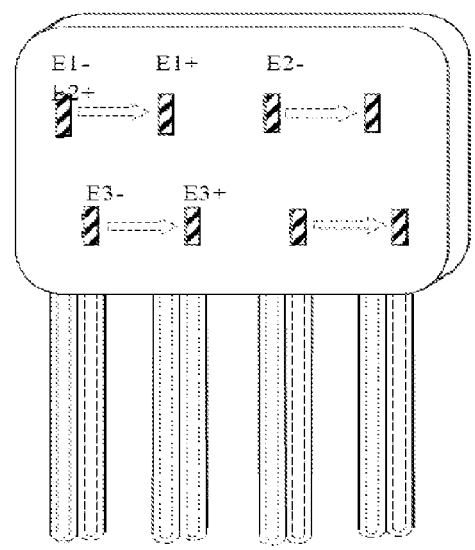

FIG. 7C shows an electrode structure 90 according to another embodiment. Electrode structure 90 comprises a flexible sheet 94 that supports four pairs of electrodes 92. Sheet 94 may comprise a thin flexible silicone sheet, for example. Electrical leads 93 are provided to connect corresponding electrodes 92 to a signal source. Electrodes and electrode leads may be of any suitable shape and material; e.g., stainless steel or platinum-iridium multi-stranded wire with Teflon™ coated leads. In the illustrated embodiment, electrode contact surfaces are exposed through electrode windows in which insulation of the leads is not present. Electrodes 92A and 92E; 92B and 92F; 92C and 92G; and 92D and 92H may be paired, for example, as shown in FIG. 7D. As another example, electrodes 92A and 92B; 92C and 92D; 92E and 92F; and 92G and 92H may be paired as shown in FIG. 7E.

Electrode structure 90 may be applied to stimulate a nerve or nerves by inserting electrode structure 90 into a blood vessel with electrodes 92 facing outwardly; and connecting any two electrodes 92 to the negative and positive outputs of a standard constant-current or constant-voltage nerve stimulator. An effective mode of stimulation is to select a pair of electrodes that are aligned along a line that is generally parallel to the target nerve, such that the greatest potential difference during stimulation will be generated along the nerve axons in the target nerve. Since the target nerve and target blood vessel may not be strictly parallel to one another, it is useful to have multiple electrodes in an electrode structure from which the pair of electrodes that provide the greatest stimulation selectivity for a target nerve can be identified by trial and error.

Figure 7F:
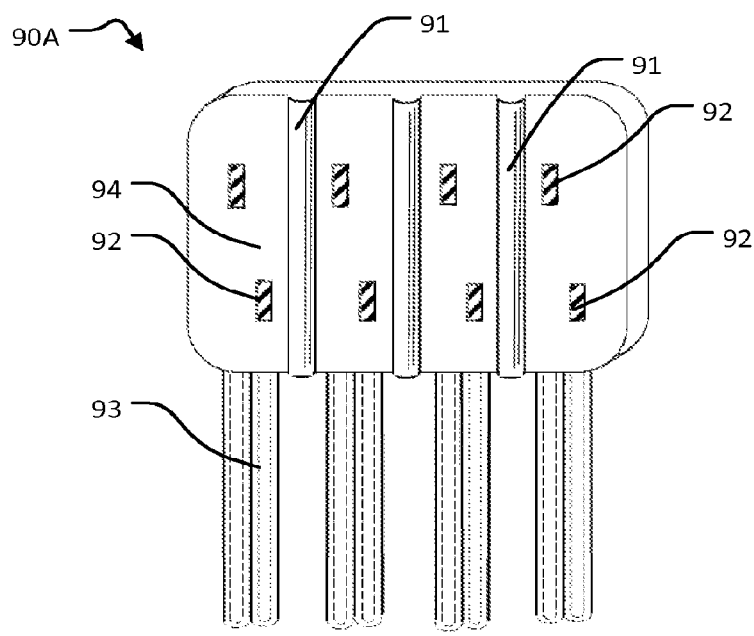

FIG. 7F shows an electrode structure 90A that is like electrode structure 90 except that it includes ridges 91 of electrically-insulating material that extend between groups of electrodes 92.

Figure 7G:
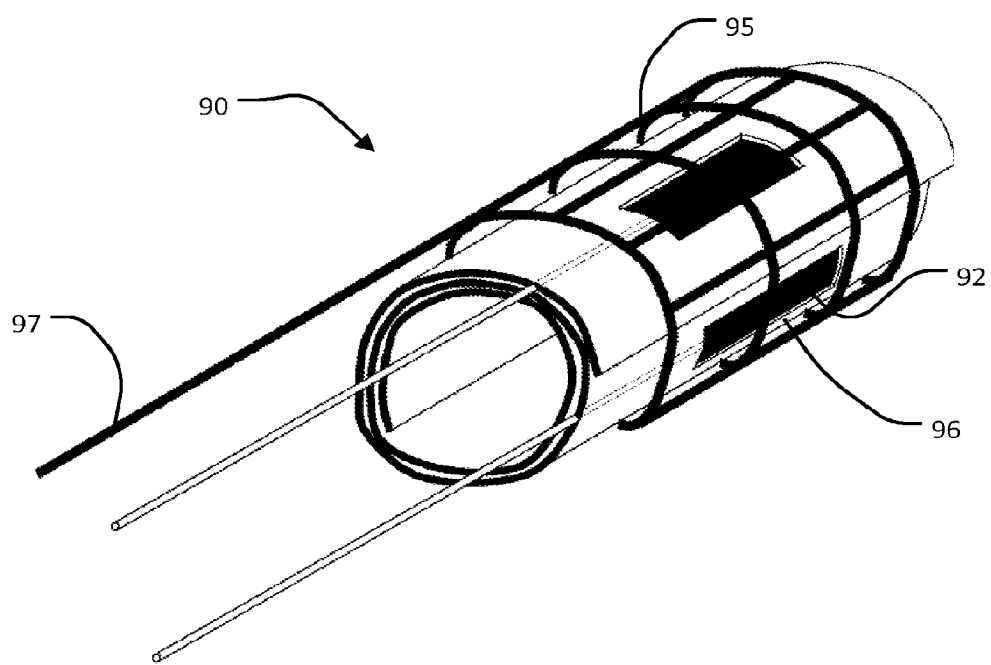
FIG. 7G is a perspective view showing an electrode structure having four rows of electrodes in a rolled configuration in which the electrode structure is curled up within an apertured insertion tube.

FIG. 7G shows an electrode structure like electrode structure 90 prepared for insertion into a blood vessel. Electrode structure 90 is rolled up into a spiral and held by an outside retainer 95. Outside retainer 95 has relatively thin walls. For example, the wall thickness may be about ½ mm or less in some embodiments. Apertures 96 penetrate the wall of outside retainer 95 and allow flow of electrical currents. Apertures 96 could optionally be filled with electrically-conducting plugs.

At least one electrode 92 of electrode structure 90 is electrically exposed to the surroundings through an aperture 96. As the electrode structure is being advanced toward an intravascular target location (the target location may be determined in advance from an imaging survey study for each patient, and monitored with fluoroscopy during the ECS implant procedure), electrodes 92 are energized. Since at least some electrodes 92 are exposed by way of apertures 96 the target nerve will be stimulated when electrode structure 90 is close enough to the target nerve. An effect of stimulation of the target nerve can be watched for in order to determine when electrode structure has reached the vicinity of the target nerve. The response may be monitored to fine tune the position of electrode structure 90 in a blood vessel. Outside retainer 95 may be removed when electrode structure 90 is at the target location. Outside retainer 95 is tethered by a tether 97 so that it can be recovered after deployment of structure 90.

Figure 7H:
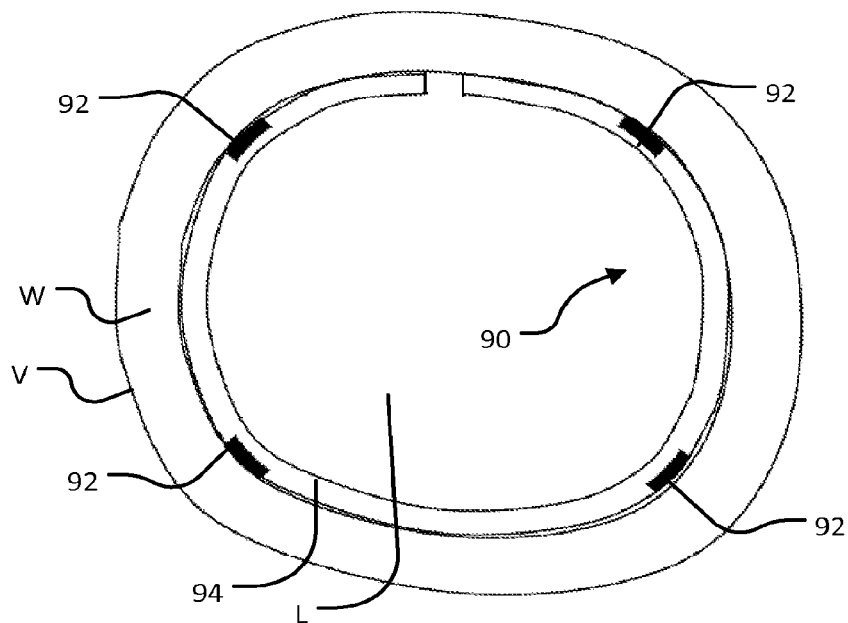
FIG. 7H is a cross section through a blood vessel within which an electrode structure according to another embodiment has been placed.

FIG. 7H shows structure 90 at its intended location in blood vessel V. Outer retainer 96 has been removed and the structure 90 has been allowed to unwind and deploy against the inside wall of blood vessel V. The width (circumferential dimension) of structure 90 is chosen to closely match the inside perimeter of blood vessel V at the target location. The inside dimension of the blood vessel V may have been previously determined from ultrasound imaging, balloon catheter, magnetic resonance imaging or other non-invasive or minimally-invasive imaging technique.

When electrode structure 90 is at its desired position for optimal stimulation of the target nerve, the outer retainer 95 is gently removed and withdrawn from the patient's body while structure 90 is kept in place, if needed, by means of a semi-rigid rod-like tool (not shown) that is temporarily used to stabilize structure 90 and prevent it from moving while outer retainer 95 is withdrawn. As the outer retainer 95 is withdrawn, structure 90 will naturally and rapidly unwrap toward its preferred enlarged-cylindrical (or near-planar in some embodiments) configuration and will stretch out against the inside wall of the blood vessel with electrodes 92 disposed outwardly in close contact to the blood vessel wall.

As noted above, the choice of electrodes to use to stimulate a target nerve can depend on the orientation of the target nerve relative to the blood vessel in which an electrode structure is deployed. Where a target nerve passes more or less at right angles to a blood vessel, it can be most efficient to stimulate the target nerve by passing electric current between two electrodes that are spaced apart circumferentially around the wall of the blood vessel. In such cases it may be desirable to provide elongated electrodes that extend generally parallel to the blood vessel (e.g. generally parallel to an axis of curvature of the electrode structure). Such elongated electrodes may be emulated by a row of smaller electrodes that are electrically connected together.

Figure 8A:
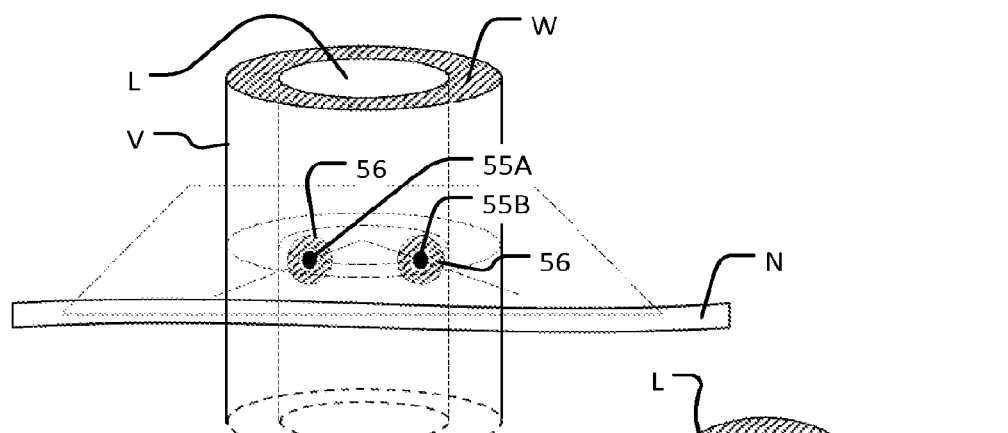
FIGS. 8A and 8B are schematic illustrations of the use of a structure comprising bi-polar electrodes to stimulate a nerve extending transversely to a blood vessel.
Figure 8B:
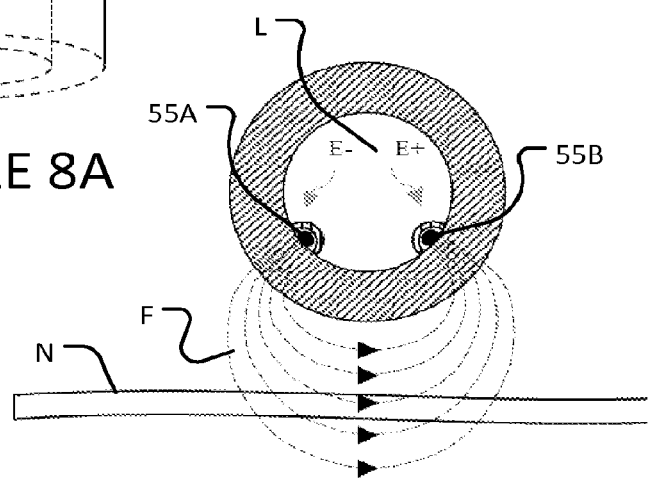

FIGS. 8A and 8B show a nerve N extending transversely to a blood vessel V. In the illustrated embodiment, the nerve extends generally at right angles to the blood vessel. An electrode structure 54 comprising first and second electrodes 55A and 55B (collectively electrodes 55) is located in lumen L of blood vessel V. Electrodes 55 are each close to or pressed against the inner face of wall W of blood vessel V. Electrode structure 54 may have additional electrodes as well as other features such as a structure for holding electrodes 54 in place however these are not shown in FIG. 8A or 8B for clarity. Electrodes 55A and 55B are spaced apart from one another in a circumferential direction around the periphery of blood vessel V. Electrodes 55 are ideally disposed in a plane in which nerve N lies and which intersects blood vessel V perpendicularly. Precise placement of the electrodes in such a configuration is not mandatory. Electrodes 55 are spaced apart in a direction that is generally along an axis of nerve N.

Each electrode 55 is protected against electrical contact with the blood in lumen L of blood vessel V by an insulating backing member 56. In the illustrated embodiment, backing members 56 comprise hollow insulating caps that may, for example, have the form of hollow hemispheres. An edge of each insulating cap contacts wall W of blood vessel V around the periphery of the corresponding electrode 55.

In this embodiment, electrodes 55 are connected in a bi-polar arrangement such that one electrode acts as a current source and the other acts as a current sink. It is not mandatory that the polarities of electrodes 55 always stay the same. For example, in some stimulation modes the polarities could be switched. In the illustrated embodiment, electrode 55A is connected as a cathode (negative) electrode while electrode 55B is connected as an anode (positive) electrode to a signal source (not shown in FIG. 8A or 8B). When a stimulation signal is applied between electrodes 55 an electric field is created. The electric field causes small electrical currents to flow between electrodes 55 by way of the surrounding tissues.

Since electrodes 55 are insulated from the lumen of blood vessel V, electric current flows out of the current source electrode 55A through wall W and surrounding tissues and returns to the current sink electrode 55B. The stimulation current flows longitudinally through the nerve N in the direction shown by arrows F. For stimulation pulses of sufficient duration and intensity, the nerve axons in target nerve N will generate action potentials that will be conducted along the stimulated axons in nerve N.

Where a target nerve extends generally parallel to a blood vessel it can be efficient to stimulate the target nerve by passing electric current between two electrodes that are spaced apart longitudinally along the wall of the blood vessel.

Figure 8C:
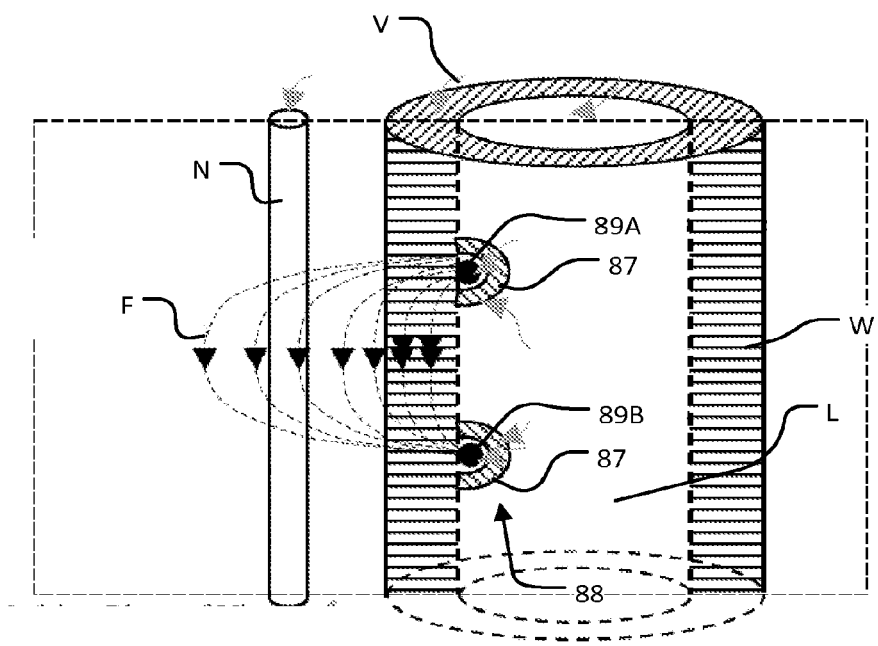
FIG. 8C is a schematic illustrations of the use of a structure comprising bi-polar electrodes to stimulate a nerve extending generally parallel to a blood vessel.

FIG. 8C shows a nerve N extending parallel to a blood vessel V. An electrode structure 88 having first and second electrodes 89A and 89B (collectively electrodes 89) is located inside blood vessel V with electrodes 89A and 89B close to, preferably against the inside of the wall W of blood vessel V. Electrode structure 88 may have additional electrodes as well as other features such as a structure for holding electrodes 89 in place however these are not shown in FIG. 8C for clarity. Electrodes 89A and 89B are spaced apart from one another in a longitudinal direction along blood vessel V. The electrodes are ideally disposed on a line extending parallel to an axis of the blood vessel although precise placement of the electrodes in such a configuration is not mandatory.

In this embodiment, electrodes 89A and 89B are connected in a bi-polar arrangement such that one electrode acts as a current source and the other acts as a current sink. It is not mandatory that the polarities of electrodes 89A and 89B always stay the same. For example, in some stimulation modes the polarities could be switched.

In the illustrated embodiment, electrode 89A is connected as a cathode (negative) electrode while electrode 89B is connected as an anode (positive) electrode to a signal source (not shown in FIG. 8C). Each electrode 89 is protected against electrical contact with the blood in lumen L of blood vessel V by an insulating backing member 87. In the illustrated embodiment, the backing members comprise hollow insulating caps that may, for example, have the form of hollow hemispheres. An edge of each insulating cap contacts the wall of blood vessel V around the periphery of the corresponding electrode 89.

Since electrodes 89 are electrically insulated from the blood in lumen L of blood vessel V, electric current flows out of the current source (e.g. cathode 89A), through wall W and eventually returns to the current sink (e.g. anode electrode 89B). This results in a stimulation current that flows longitudinally through nerve N in the direction shown by arrows F. For stimulation pulses of sufficient duration and intensity, the nerve axons in the target nerve will generate action potentials that will be conducted along the stimulated axons in nerve N.

Stimulating the phrenic nerves to regulate or cause breathing is an example application of electrode structures as described herein. The present invention provides a surgically simple, lower risk response to the need of stimulating the phrenic nerves to control the movement of the diaphragm and restore normal breathing rate in people who have lost control of diaphragm due to a central neurological lesion such as a high cervical spinal cord injury or disease, including quadriplegia; central alveolar hypoventilation; decreased day or night ventilatory drive (e.g. central sleep apnea, Ondine's Curse) or brain stem injury or disease. Phrenic nerves may be stimulated on an acute care or chronic basis.

The phrenic nerves provide the major nerve supply to the diaphragm. Each phrenic nerve contributes predominantly motor fibres solely to its hemidiaphragm. The passage taken by the right and left phrenic nerves through the thorax is different. This is largely due to the disposition of great vessels within the mediastinum. Occasionally, the phrenic nerve may be joined by an accessory phrenic nerve.

The phrenic nerve on both sides originates from the ventral rami of the third to fifth cervical nerves. The phrenic nerve passes inferiorly down the neck to the lateral border of scalenus anterior. Then, it passes medially across the border of scalenus anterior parallel to the internal jugular vein which lies inferomedially. At this point the phrenic nerve is deep to the prevertebral fascia, the transverse cervical artery and the suprascapular artery.

At the anterior, inferomedial margin of scalenus anterior and hence superficial to the second part of the right subclavian artery, the right phrenic nerve passes medially to cross the pleural cupola deep to the subclavian vein. More medially, it crosses the internal thoracic artery at approximately the level of the first costochondral junction.

Within the thorax the right phrenic nerve is in contact with mediastinal pleura laterally and medially, in succession from superior to inferior, the following venous structures: right brachiocephalic vein, superior vena cava, pericardium of the right atrium, inferior vena cava. From the level of the superior vena cava it is joined by the pericardiophrenic artery and both run inferiorly anterior to the lung root. The right phrenic nerve pierces the diaphragm in its tendinous portion just slightly lateral to the inferior vena caval foramen. It then forms three branches on the inferior surface of the diaphragm: anterior, lateral and posterior. These ramify out in a radial manner from the point of perforation to supply all but the periphery of the muscle.

At the anteroinferior medial margin of scalenus anterior, the left phrenic nerve crosses the first part of the left subclavian artery and then the internal thoracic artery sited slightly inferiorly. Passing inferiorly with the internal thoracic artery laterally, it lies deep to the left brachiocephalic vein and the left first costochondral joint. It receives a pericardiophrenic branch of the internal thoracic artery which stays with its distal course.

Within the thorax, the left phrenic nerve continues inferiorly and slightly laterally on the anterolateral aspect of the arch of the aorta, separated from the posterior right vagus nerve by the left superior intercostal vein. Then it descends anterior to the root of the left lung intermediate to fibrous pericardium medially and parietal pleura laterally. Finally, it curves inferiorly and anteriorly to reach the surface of the diaphragm which it pierces anterior to the central tendon and lateral to the pericardium. It then forms three branches on the inferior surface of the diaphragm: anterior, lateral and posterior. These ramify out in a radial manner from the point of perforation to supply all but the periphery of the muscle.

The accessory phrenic nerve on each side occurs in roughly 15-25% of people. It originates as a branch of the fifth cervical nerve which would otherwise pass to the subclavius. The accessory phrenic nerve begins lateral to the phrenic nerve in the neck and obliquely traverses the anterior surface of scalenus anterior as it descends. It joins the phrenic nerve at the root of the neck to descend to the diaphragm.

Figure 9:
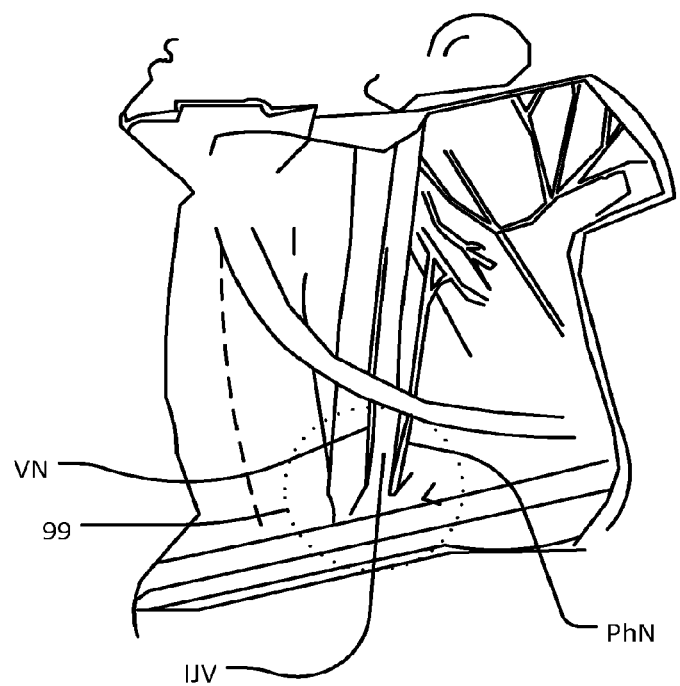
FIG. 9 is a cut away view of a person's neck.

FIG. 9 shows the anatomy of the neck and, in particular, the relative locations of phrenic nerve (PhN), vagus nerve (VN) and internal jugular vein (IJV). Note that the IJV courses between the PhN and VN. The PhN merges with the IJV and the three structures run together distally at level of the clavicle (indicated by circle 99).

Figure 9A:
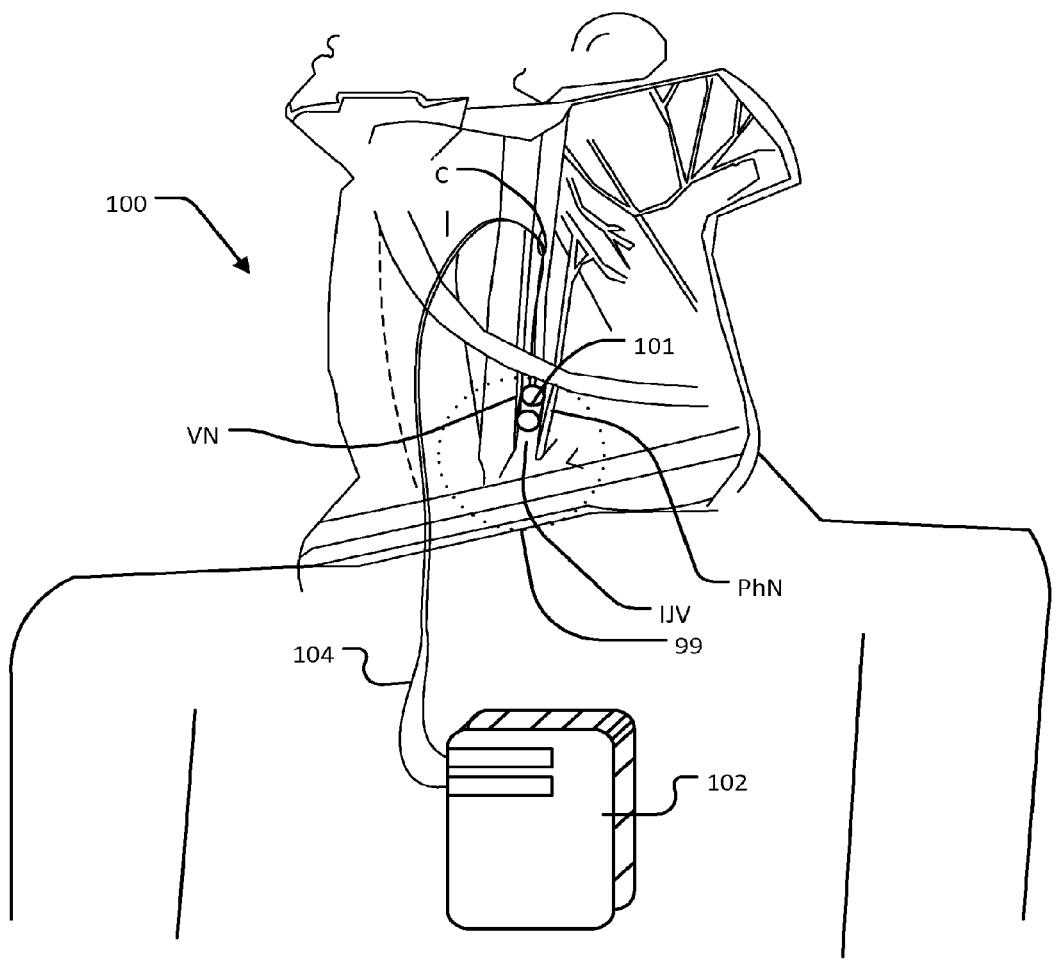
FIG. 9A is a cut away view illustrating a minimally invasive transvascular nerve stimulation system installed in a person according to an embodiment wherein an electrode structure is disposed in the person's internal jugular vein in the neck or upper chest region.

In one example embodiment illustrated in FIG. 9A, a minimally invasive nerve stimulation system ('MINS') 100 comprising a flexible intravascular electrode array 101, for example, an electrode structure of one of the embodiments described above is permanently placed inside a target blood vessel V (in this example the left Internal Jugular Vein, IJV) in close proximity to a target nerve (in this example the left phrenic nerve PhN). One or more electrodes of the electrode array is disposed for selective stimulation of the PhN. Other electrodes are optionally disposed for selective stimulation of a second target nerve, in this example the left vagus nerve VN.

The electrode leads 104 from electrode array 101 emerge from the cannulated BV at the original venous penetration site, C, and then course subcutaneously to connectors 105 that connect to the header of an implanted pulse generator 102 that is surgically placed in a standard subcutaneous pocket. The pocket may be in the upper chest wall for example. FIG. 9 shows only one electrode array 101 on the left side of the neck.

In this embodiment, the implanted MINS 100 stimulates the left PhN to assist breathing by causing rhythmic inspiratory movements of the diaphragm muscle (not shown in FIG. 9). Another electrode array may additionally be implanted in a blood vessel on the right side of the patient's body. For example, another electrode array 101 may be implanted in the right internal jugular vein for selective stimulation of the right PhN and, optionally, also the right VN, if so desired. The additional electrode array may be connected to internal pulse generator 102 or to a second internal pulse generator (not shown in FIG. 9).

MINS 100 may be installed percutaneously using standard procedures for the installation of deep catheters, cannulas, leads or other intravascular device. Such procedures are described in the medical literature. Once an electrode array has been introduced to a location near the target location in the internal jugular vein then the position of the electrode array may be fine-tuned by applying low-current stimulation signals to one or more of the electrodes in electrode array 101 and observing the patient's breathing.

Figure 10A:
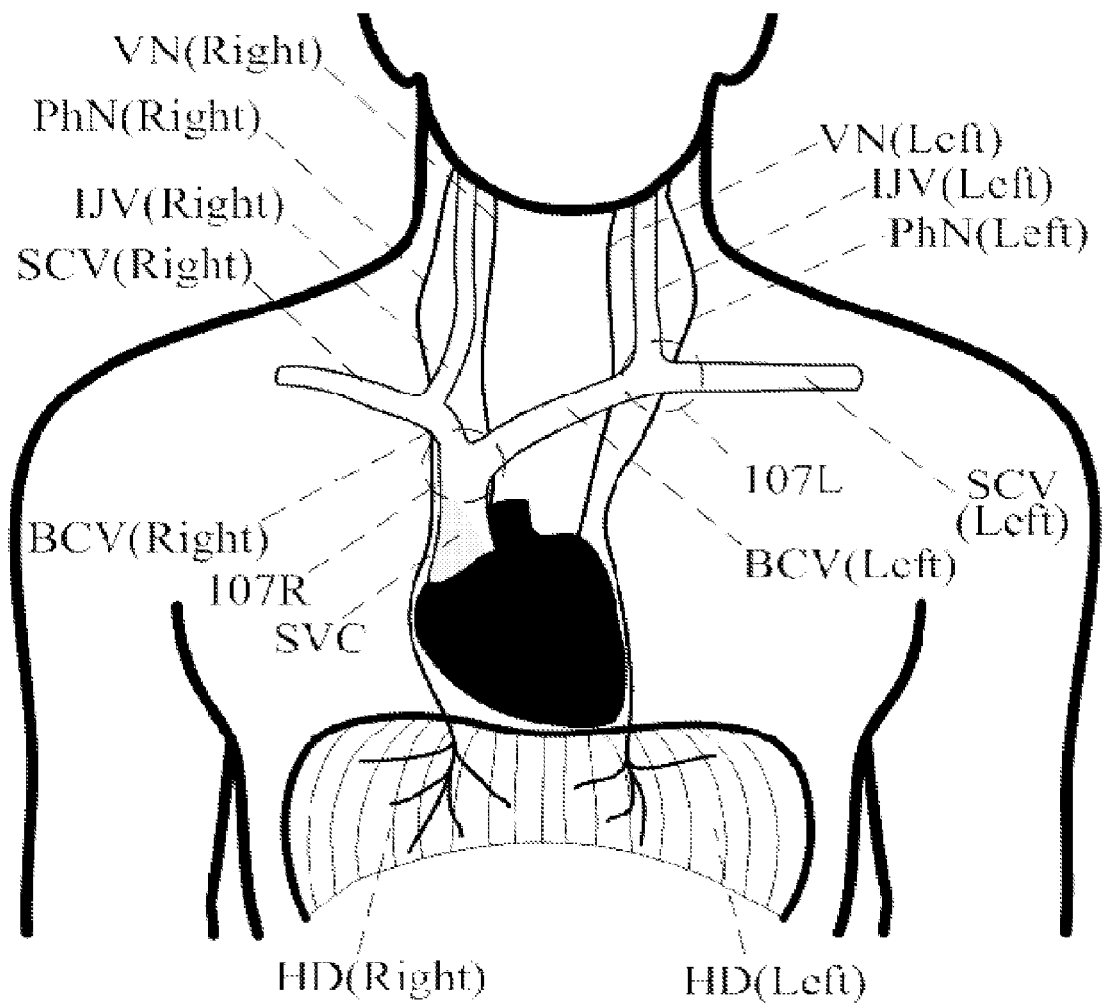
FIGS. 10A and 10B illustrate the anatomy of selected nerves and blood vessels in a person's neck and upper torso.
Figure 10B:
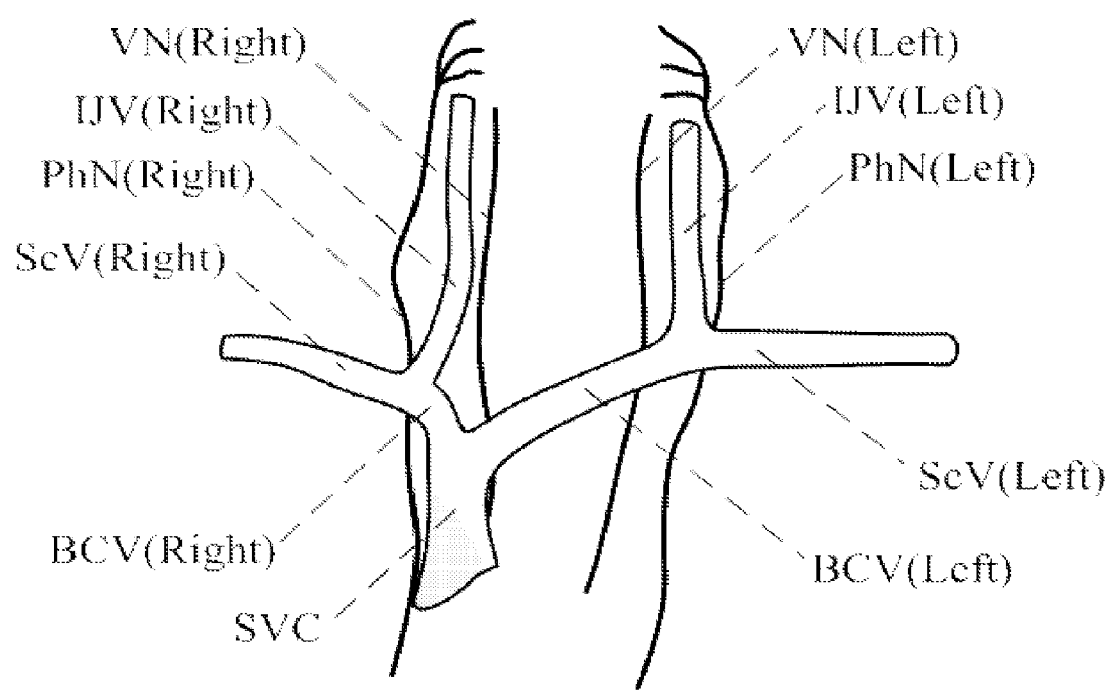

FIGS. 10A and 10B illustrate the anatomy of the neck and chest and, in particular, the relative locations of the left and right phrenic nerves (PhN), vagus nerves (VN), internal jugular veins (IJV), brachiocephalic veins (BCV), subclavian veins (SCV) and superior vena cava (SVC). The PhNs run approximately perpendicular to and close to the BCVs in areas 107R and 107L near the IJV/BCV junctions.

Each PhN may have more that one branch. The branches may join together at variable locations ranging from the neck region to the chest region below the IJV/BCV junctions. In the latter case, branches of the PhN on either side of the body may course on opposite sides of the BCVs. Two branches of the right PhN are labeled PhN-1 and PhN-2 in FIG. 10B. The right PhN may include branches that course on either side of the SVC. The left and right PhN extend respectively to left and right hemi-diaphragms (HD).

Figure 11:
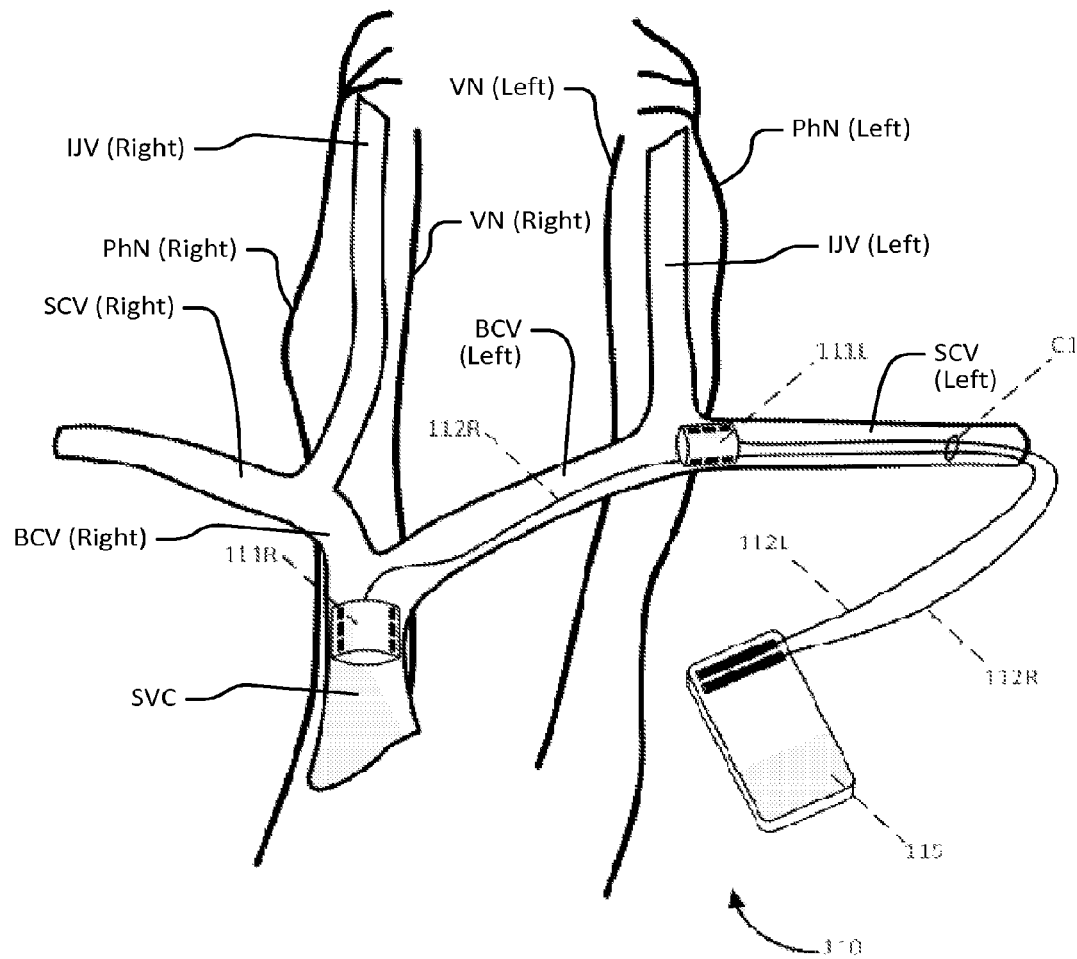
FIG. 11 is a cut away view illustrating a minimally invasive transvascular nerve stimulation system installed in a person according to an embodiment wherein electrode structures are disposed in one or both of the person's superior vena cava and left subclavian vein.

FIG. 11 shows a MINS 110 having electrode structures 111L and 111R (collectively 111) located respectively in a patient's left SCV and SVC vessels near the left- and right-PhN respectively. Leads 112L and 112R (collectively 112) respectively connect the electrodes of left- and right-electrode structures 111L and 111R to a signal generator. In the illustrated embodiment, the signal generator comprises an implantable pulse generator (IPG) 115. Alternatively, as described above, some or all functions of pulse generator 115 may be provided by circuitry that is co-located with or integrated with one or both of electrode structures 111. In some embodiments, pulse generator 115 generates control signals that are transmitted by way of a wireless communication link to cause circuitry that is local to electrode structures 111 to apply stimulation pulses by way of electrodes on electrode structures 111.

The implantable pulse generator may be configured to deliver electrical pulses to electrodes of the left- and right electrode structures 111 more-or-less simultaneously so that the left- and right-hemidiaphragms are induced to undergo breathing motions in a synchronized manner. IPG 115 may, for example, apply bursts of stimulus pulses at a rate of about 12 or 13 bursts per minute. Each burst may, for example, comprise 20-40 current pulses delivered at a rate of 20 Hz or so and last roughly 1 to 2 seconds. Each burst induces signals in the phrenic nerve that cause the diaphragm to move to provide inspiration. Expiration occurs between bursts.

MINS 110 can be readily installed as shown in FIG. 11. Electrode structures 111R and 111L may both be introduced through the same intravascular insertion point C1 in the left SCV. In some embodiments, electrode structure 111L is installed first. In such embodiments, electrode structure 111L can be passed through the left SVC past electrode structure 111L (e.g. through a bore of electrode structure 111L) to its target location in the SVC. Flexible leadout cable 112R passes through electrode structure 111L. Both leadout cables 112 emerge from the SCV and course subcutaneously to a subcutaneous pocket area in the upper chest where the leadout cable connectors are connected to IPG 115.

Locating initial target positions for electrode structures 111 is facilitated because the SVC, heart and BCV can be readily visualized using available imaging techniques. It is known that the phrenic nerves pass tightly past the heart on each side. Therefore, target locations in the blood vessels within ±1 to 2 cm of the optimum positions for stimulating the phrenic nerves can be determined readily from images of the upper chest and lower neck.

The arrangement shown in FIG. 11 has the advantage that the distance from electrode structures 111 to the target nerves in these locations may be smaller, more uniform and more reproducible than for similar electrodes implanted in more proximal locations in the IJVs where the target PhNs run parallel to the IJVs, but at more variable distances (see FIG. 9, for example).

MINS 110 may be varied by leaving out one of electrode structures 111 and its associated cable 112. Such embodiments may be useful in acute care environments where it is necessary to provide breathing assistance using a simple quick procedure. Such embodiments may also be useful in chronic situations where stimulation of one hemi-diaphragm is sufficient. Where only one electrode structure 111 is implanted, the electrode structure may be at either the location of electrode structure 111R or the location of electrode structure 111L.

Figure 12:
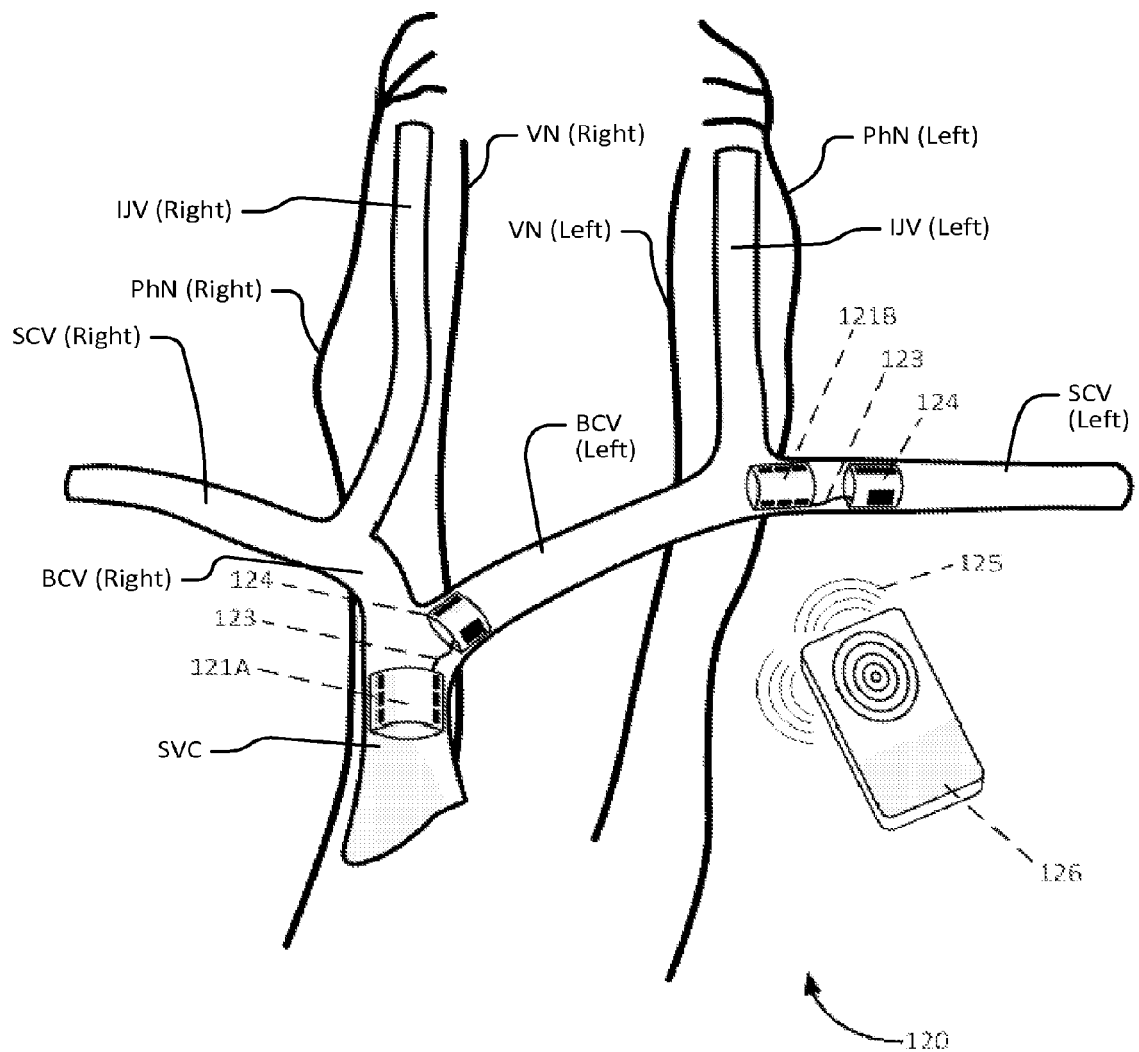
FIG. 12 is a cut away view illustrating a minimally invasive transvascular nerve stimulation system installed in a person according to an embodiment wherein control signals are transmitted wirelessly to cause stimulation signals to be delivered at electrode structures.

FIG. 12 shows a minimally-invasive nerve stimulation system 120 that is like MINS 110 of FIG. 11 but provides a wireless connection between an implantable pulse generator and circuits which deliver stimulation signals to electrodes. System 120 has two sets of intravascular electrodes 121A and 121B. In some embodiments, each set of electrodes comprises an electrode structure as described herein. Each set of electrodes 121A and 121B is connected by short flexible lead wires 123 to an associated RF receiver unit 124. RF receiver units receive wireless stimulation commands 125 from an implanted pulse generator 126 having an associated transmitter (which is built into implantable pulse generator 126 in the illustrated embodiment.

Each receiver unit 124 may comprise a hermetic package containing an antenna and circuitry to decode command signals and deliver stimulation pulses to the electrodes of the corresponding electrode array 121. Each receiver unit may be attached to an autonomous stent-like structure for safe, permanent and stable installation in a blood vessel near the associated electrode array 121. The receiver units may be powered by the RF signal received from implantable pulse generator 126. In such cases, the receiver units do not require internal batteries.

Implantable pulse generator 126 may contain batteries or another source of electrical energy, control circuitry and transmitter antennas to communicate with receiver units 124 and with an external programmer (not shown) that allows a therapist to program the implanted system.

In some embodiments, an implantable pulse generator or other signal source may have a primary battery or a rechargeable battery that can be periodically recharged through the patient's skin. In either case, it is desirable that the battery or other source of electrical power have an expected life span such that it will not require replacement for a reasonable period such as at least about 3 to 5 years.

Methods of stimulating the phrenic nerves, as described herein can have the advantages that:
  electrodes do not come into contact with the delicate phrenic nerves;
  there is no implanted structure that interferes with movement of the diaphragm;
  the system may be implanted and self-contained such that no wires cross the skin;
  access to both the right and left phrenic nerves can be provided through a single point of entry;
  a control system, such as an implantable pulse generator may be placed in reasonably close proximity to an electrode structure so as to facilitate wireless control over the delivery of stimulation pulses at the electrode structure by the implantable pulse generator.

The applications of the apparatus and methods described herein are not limited to phrenic and vagus nerves. The apparatus and methods described herein may be applied to provide surgically simple, low risk solutions for stimulating a wide range of peripheral or cranial nerves. For example, the methods and apparatus may be applied to stimulate the obturator nerve in the hip/groin area or the trigeminal nerve in the head.

The apparatus and methods may be applied to treatment of a wide variety of disorders such as pain of peripheral or craniofacial origin, sensory deficits, paralysis or paresis of central origin, autonomic disorders, and generally any medical condition that can be treated or alleviated using neuromodulation by electrical stimulation of a nerve that is in close proximity to a larger blood vessel into which a flexible multi-channel electrode array can be deployed.

Advantageously, implantation of electrode structures in blood vessels is reversible and does not require surgical intervention directly involving the target nerves.

In some embodiments, signal generator 115 has sensors that sense a condition of the patient and adjust stimulation of the phrenic nerve based on input from the sensors. The sensors may detect things such as one or more of:
  whether the patient is speaking or preparing to speak;
  whether the patient is lying down or sitting or standing;
  whether the patient is awake or asleep;
  blood oxygen concentration;

blood $CO_2$ concentration;
etc.

In response to the sensor signals, the signal generator may adapt the pattern or rate of breathing. For example:

Breathing could be automatically suppressed when a sensor signal indicates that the patient is attempting to speak.

A breathing rate could be increased during periods of increased physical activity or low blood oxygen concentration.

A breathing rate could be decreased or regularized during periods of relaxation or sleep.

On-demand breathing stimulation could be provided in response to the detection of the onset of irregular breathing during sleep.

The sensors may be built into the signal generator. For example, the signal generator may include:

accelerometers and processor logic configured to determine from outputs of the accelerometers whether the patient's motions indicate that the patient is awake or asleep;

an inclinometer or accelerometer and processor logic configured to determine from one or more outputs of the inclinometer of accelerometer whether the patient is lying or upright.

Other sensors may be implanted. For example, in some embodiments, a blood chemistry sensor such as a blood oxygen sensor and/or a blood $CO_2$ sensor is implanted at a suitable location in the patient. The blood oxygen monitor may be mounted on an electrode structure 111 for example. Other sensors may sens signals in the patient's nerves.

Where a component (e.g. an electrode, signal generator, lead, stent, assembly, device, antenna, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example, electrodes on an electrode structure may be arranged to provide unipolar, bipolar, tripolar or balanced tripolar electrode arrangements or combinations thereof. The example embodiments described herein include various features such as different geometries for insulating backing sheets, different arrangements of electrodes, different control arrangements, and the like. These features may be mixed and matched (i.e. combined on additional combinations) in other embodiments of the invention. Accordingly, the scope of the invention is to be construed in accordance with the substance defined by the following claims.

What is claimed is:

1. A system for stimulating a phrenic nerve of a patient, the system comprising:
    a signal generator to produce stimulation signals;
    a lead structure configured for insertion into a venous system of the patient, the lead structure having a plurality of leads to receive stimulation signals from the signal generator;
    an array of electrodes on the lead structure positionable proximate the phrenic nerve and configured to receive stimulation signals from at least one of the plurality of leads for stimulation of the phrenic nerve, wherein the array of electrodes includes more than two electrically discrete electrodes; and
    a control system programmed to select a bipolar pair of electrodes from the array of electrodes, the pair of electrodes including two electrodes having a stimulation efficacy for the phrenic nerve that is greater than a stimulation efficacy of other pairs of electrodes of the array of electrodes, wherein the two electrodes are configured to align substantially parallel to the phrenic nerve.

2. The system of claim 1, further comprising a breathing sensor.

3. The system of claim 2, wherein the breathing sensor is configured to sense breathing of the patient, and wherein the signal generator adjusts at least one of a rate and a pattern of the stimulation signals based on the sensed breathing.

4. The system of claim 2, wherein the breathing sensor is configured to detect irregular breathing of the patient.

5. The system of claim 1, further comprising a motion sensor.

6. The system of claim 5, wherein the motion sensor is configured to sense motion of the patient, and wherein the motion sensor is at least one of an accelerometer or an inclinometer.

7. The system of claim 6, wherein the control system is further configured, based on the sensed motion, to determine a sleep state of the patient.

8. The system of claim 6, wherein the control system is further configured, based on the sensed motion, to determine a position of the patient.

9. The system of claim 1, wherein the control system is programmed to select any two electrodes of the array of electrodes for stimulation of the phrenic nerve.

10. The system of claim 1, wherein the array of electrodes is configured to be positioned in at least one of a superior vena cava or a right jugular vein for stimulation of a right phrenic nerve.

11. The system of claim 1, wherein each electrode of the array of electrodes is electrically exposed on an outer surface of the lead structure through a de-insulated portion of the lead structure.

12. The system of claim 1, wherein the array of electrodes includes a plurality of electrode pairs arranged in at least two rows, the at least two rows extending parallel to a longitudinal axis of the lead structure.

13. The system of claim 1, wherein the control system is programmed to select the pair of electrodes by determining that the pair of electrodes has a stimulation efficacy for the phrenic nerve that is greater than a stimulation efficacy of any of the other pairs of electrodes.

14. The system of claim 1, wherein each electrode of the array of electrodes includes an insulating material on a side of the electrode facing an interior of the lead structure.

15. The system of claim 1, wherein the pair of electrodes is configured to emit an electrical field extending radially outwards from only a portion of a circumference of the lead structure.

16. The system of claim 1, wherein the bipolar pair of electrodes are configured to stimulate a sector of tissue that extends radially outward from a superior vena cava and spans an angle about the superior vena cava less than a full circumference of the superior vena cava.

17. The system of claim 1, wherein the bipolar pair of electrodes include a current source and a current sink.

18. The system of claim 1, wherein the array of electrodes is configured to be positioned in at least one of a left jugular vein and a left subclavian vein for stimulation of a left phrenic nerve.

19. The system of claim 1, wherein a first electrode of the bipolar electrode pair is positioned at a first radial position on the lead structure, and a second electrode of the bipolar pair is positioned at a second radial position on the lead structure.

20. A system for stimulating a phrenic nerve of a patient, the system comprising:
- a signal generator to produce stimulation signals;
- a lead structure configured for insertion into a venous system of the patient, the lead structure having a plurality of leads to receive stimulation signals from the signal generator;
- an array of electrodes on the lead structure positionable proximate the phrenic nerve and configured to receive stimulation signals from at least one of the plurality of leads for stimulation of the phrenic nerve, wherein the array of electrodes includes more than two electrically discrete electrodes, and wherein each electrode of the array of electrodes is positioned radially inwards of an outer non-conductive portion of the lead structure and is exposed through an opening in the outer non-conductive portion; and
- a control system programmed to select a bipolar pair of electrodes from the array of electrodes, the pair of electrodes including two electrodes configured to align substantially parallel to the phrenic nerve.

21. The system of claim 20, further comprising a breathing sensor.

22. The system of claim 20, further comprising a motion sensor.

23. The system of claim 20, wherein the array of electrodes is configured to be positioned in a superior vena cava for stimulation of a right phrenic nerve.

24. The system of claim 20, wherein the control system is programmed to select the pair of electrodes by determining that the pair of electrodes has a stimulation efficacy for the phrenic nerve that is greater than a stimulation efficacy of other pairs of electrodes of the array of electrodes.

* * * * *